United States Patent
Popp et al.

(10) Patent No.: US 8,764,922 B2
(45) Date of Patent: *Jul. 1, 2014

(54) METHOD OF MANUFACTURING A BODY ADHERING ABSORBENT ARTICLE ORIENTATED IN THE MACHINE DIRECTION WITH REDUCED CURL

(75) Inventors: Robert Lee Popp, Greenville, WI (US); Jay David Gottleib, Oshkosh, WI (US); Joseph Daniel Coenen, Kaukauna, WI (US); Gary Alan Turchan, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 495 days.

This patent is subject to a terminal disclaimer.

(21) Appl. No.: 13/022,700

(22) Filed: Feb. 8, 2011

(65) Prior Publication Data

US 2012/0199267 A1    Aug. 9, 2012

(51) Int. Cl.
*B32B 37/00* (2006.01)

(52) U.S. Cl.
USPC .......... 156/73.1; 156/164; 156/229; 156/267; 156/269

(58) Field of Classification Search
USPC ........ 156/73.1, 160, 163, 164, 183, 229, 324, 156/494, 495, 496, 553, 555, 580.1, 580.2, 156/582, 583.1, 250, 267, 269
See application file for complete search history.

(56) References Cited

U.S. PATENT DOCUMENTS

| | | |
|---|---|---|
| 2,720,477 A | 10/1955 | Lancaster |
| 2,862,846 A | 12/1958 | Blackford et al. |
| 3,338,992 A | 8/1967 | Kinney |
| 3,341,394 A | 9/1967 | Kinney |
| 3,502,538 A | 3/1970 | Petersen |

(Continued)

FOREIGN PATENT DOCUMENTS

| | | |
|---|---|---|
| EP | 0 638 303 B1 | 11/1997 |
| EP | 0 850 628 A1 | 7/1998 |

(Continued)

OTHER PUBLICATIONS

American Society for Testing Materials (ASTM) Designation: D1300-53 T, "Tentative Specifications and Methods of Test for Laminated Thermosetting Decorative Sheets," pp. 148-166, issued 1953.

(Continued)

*Primary Examiner* — James Sells
(74) *Attorney, Agent, or Firm* — Kimberly-Clark Worldwide, Inc.

(57) ABSTRACT

The present disclosure provides methods of manufacturing a body adhering absorbent article oriented in the machine direction wherein the body adhering absorbent articles have reduced or eliminated curl. The articles are manufactured with reduced curl by selectively reducing or eliminating the shell elastic tension in regions where components of the body adhering absorbent article are to be attached to form the composite absorbent article web. In certain aspects the body adhering absorbent articles are manufactured by supplying an elastic web of shell material having a longitudinal and transverse direction, stretching the web of shell material in the longitudinal direction, deadening at least one region of the stretched web of shell material, attaching at least one absorbent article component to at least a portion of the longitudinal deadened zone to form a composite web material, and cutting the composite web material to form a body adhering absorbent article.

8 Claims, 14 Drawing Sheets

(56) References Cited

U.S. PATENT DOCUMENTS

| | | | |
|---|---|---|---|
| 3,502,763 A | 3/1970 | Hartmann |
| 3,531,847 A | 10/1970 | Wallerstein |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,414,970 A | 11/1983 | Berry |
| 4,488,928 A | 12/1984 | Ali Khan et al. |
| 4,556,441 A | 12/1985 | Faasse, Jr. |
| 4,631,062 A | 12/1986 | Lassen et al. |
| 4,655,210 A | 4/1987 | Edenbaum et al. |
| 4,693,858 A | 9/1987 | Volke |
| 4,743,245 A | 5/1988 | Lassen et al. |
| 4,804,380 A | 2/1989 | Lassen et al. |
| 4,846,824 A | 7/1989 | Lassen et al. |
| 4,991,378 A | 2/1991 | Dotta |
| 5,059,189 A | 10/1991 | Cilento et al. |
| 5,114,419 A | 5/1992 | Daniel et al. |
| 5,147,338 A | 9/1992 | Lang et al. |
| 5,147,938 A | 9/1992 | Kuller |
| 5,194,550 A | 3/1993 | Rance et al. |
| 5,382,400 A | 1/1995 | Pike et al. |
| 5,445,627 A | 8/1995 | Mizutani et al. |
| 5,453,143 A | 9/1995 | Menard |
| 5,501,661 A | 3/1996 | Cartmell et al. |
| H1602 H | 10/1996 | Brock |
| 5,611,790 A | 3/1997 | Osborn, III et al. |
| 5,618,281 A | 4/1997 | Betrabet et al. |
| 5,658,270 A | 8/1997 | Lichstein |
| 5,662,633 A | 9/1997 | Doak et al. |
| 5,685,833 A | 11/1997 | Turngren |
| 5,759,560 A | 6/1998 | Dillon |
| 5,807,367 A | 9/1998 | Dilnik et al. |
| 5,967,009 A | 10/1999 | Truttmann et al. |
| 6,001,471 A | 12/1999 | Bries et al. |
| 6,004,253 A | 12/1999 | Riedel et al. |
| 6,045,900 A | 4/2000 | Haffner et al. |
| 6,156,818 A | 12/2000 | Corzani et al. |
| 6,169,224 B1 | 1/2001 | Heinecke et al. |
| 6,174,399 B1 | 1/2001 | Decandia et al. |
| 6,177,482 B1 | 1/2001 | Cinelli et al. |
| 6,187,989 B1 | 2/2001 | Corzani et al. |
| 6,191,189 B1 | 2/2001 | Cinelli et al. |
| 6,211,263 B1 | 4/2001 | Cinelli et al. |
| 6,213,993 B1 | 4/2001 | Zacharias et al. |
| 6,264,784 B1 | 7/2001 | Menard et al. |
| 6,279,440 B1 | 8/2001 | Truttmann et al. |
| 6,298,760 B1 | 10/2001 | Truttmann et al. |
| 6,305,260 B1 | 10/2001 | Truttmann et al. |
| 6,316,524 B1 | 11/2001 | Corzani et al. |
| 6,362,389 B1 | 3/2002 | McDowall et al. |
| 6,365,645 B1 | 4/2002 | Cinelli et al. |
| 6,369,126 B1 | 4/2002 | Cinelli et al. |
| 6,383,431 B1 | 5/2002 | Dobrin et al. |
| 6,620,143 B1 | 9/2003 | Zacharias et al. |
| 6,632,210 B1 | 10/2003 | Glasgow et al. |
| 6,641,569 B1 | 11/2003 | Coles et al. |
| 6,657,009 B2 | 12/2003 | Zhou |
| 6,670,402 B1 | 12/2003 | Lee et al. |
| 6,700,033 B1 | 3/2004 | Marcussen et al. |
| 6,765,123 B2 | 7/2004 | De Jong et al. |
| 6,960,275 B2 | 11/2005 | Vesley et al. |
| 6,977,324 B2 | 12/2005 | Serrano |
| 6,997,915 B2 | 2/2006 | Gell et al. |
| 7,045,559 B2 | 5/2006 | Yahiaoui et al. |
| 7,053,131 B2 | 5/2006 | Ko et al. |
| 7,122,022 B2 | 10/2006 | Drevik |
| 7,125,401 B2 | 10/2006 | Yoshimasa |
| 7,166,179 B2 | 1/2007 | Muesch et al. |
| 7,217,259 B2 | 5/2007 | McDaniel |
| 7,265,158 B2 | 9/2007 | Risen, Jr. et al. |
| 7,351,297 B2 * | 4/2008 | Middlesworth et al. ..... 156/73.1 |
| 7,358,282 B2 | 4/2008 | Krueger et al. |
| 7,378,450 B2 | 5/2008 | Erkey et al. |
| 7,396,975 B2 | 7/2008 | Sigurjonsson et al. |
| 7,488,186 B1 | 2/2009 | Hayakawa |
| 7,745,682 B2 | 6/2010 | Sigurjonsson et al. |
| 2001/0002289 A1 | 5/2001 | Himmelsbach et al. |
| 2001/0039407 A1 | 11/2001 | Widlund |
| 2004/0116883 A1 | 6/2004 | Krautkramer et al. |
| 2004/0151930 A1 | 8/2004 | Rouns et al. |
| 2005/0010185 A1 | 1/2005 | Mizutani et al. |
| 2005/0065491 A1 | 3/2005 | Schneider et al. |
| 2005/0124958 A1 | 6/2005 | Brisebois |
| 2005/0148984 A1 | 7/2005 | Lindsay et al. |
| 2005/0198931 A1 | 9/2005 | Cesiro et al. |
| 2006/0058764 A1 | 3/2006 | Bohlen et al. |
| 2006/0148917 A1 | 7/2006 | Radwanski et al. |
| 2006/0161125 A1 | 7/2006 | Bohlen et al. |
| 2006/0224139 A1 | 10/2006 | Erdman et al. |
| 2006/0264884 A1 | 11/2006 | Carstens |
| 2007/0100313 A1 | 5/2007 | Luizzi |
| 2007/0124850 A1 | 6/2007 | Buettner |
| 2007/0179418 A1 | 8/2007 | Ritzdorf et al. |
| 2007/0287973 A1 | 12/2007 | Cohen et al. |
| 2008/0004584 A1 | 1/2008 | Langdon et al. |
| 2008/0015535 A1 | 1/2008 | Gannon et al. |
| 2008/0057811 A1 | 3/2008 | Yahiaoui et al. |
| 2008/0207779 A1 | 8/2008 | Yahiaoui et al. |
| 2008/0241541 A1 * | 10/2008 | Conrad et al. ........... 428/402.24 |
| 2009/0036858 A1 | 2/2009 | Van Den Bogart et al. |
| 2009/0054864 A1 | 2/2009 | Lira et al. |
| 2009/0062762 A1 | 3/2009 | Himbergen et al. |
| 2009/0069771 A1 | 3/2009 | Yu et al. |
| 2009/0069780 A1 | 3/2009 | Plentovich et al. |
| 2009/0171309 A1 | 7/2009 | Vandenbogart et al. |
| 2009/0182296 A1 | 7/2009 | Dennis et al. |
| 2009/0198203 A1 | 8/2009 | Lira et al. |
| 2009/0204090 A1 | 8/2009 | Dennis et al. |
| 2009/0204092 A1 | 8/2009 | Loyd et al. |
| 2010/0057034 A1 | 3/2010 | Dennis et al. |
| 2010/0121304 A1 | 5/2010 | Zhou et al. |
| 2010/0152693 A1 | 6/2010 | Lira et al. |
| 2010/0198177 A1 | 8/2010 | Yahiaoui et al. |
| 2012/0199268 A1 * | 8/2012 | Popp et al. ................ 156/73.1 |

FOREIGN PATENT DOCUMENTS

| | | |
|---|---|---|
| EP | 1 696 853 B1 | 10/2009 |
| GB | 2 284 767 A | 6/1995 |
| JP | 04-279159 A | 10/1992 |
| WO | WO 95/16424 A1 | 6/1995 |
| WO | WO 98/27910 A1 | 7/1998 |
| WO | WO 98/27912 A1 | 7/1998 |
| WO | WO 98/27913 A1 | 7/1998 |
| WO | WO 98/27915 A1 | 7/1998 |
| WO | WO 98/27916 A1 | 7/1998 |
| WO | WO 98/27917 A1 | 7/1998 |
| WO | WO 98/27918 A1 | 7/1998 |
| WO | WO 98/28015 A1 | 7/1998 |
| WO | WO 98/28017 A1 | 7/1998 |
| WO | WO 98/28019 A1 | 7/1998 |
| WO | WO 98/28022 A1 | 7/1998 |
| WO | WO 98/28023 A1 | 7/1998 |
| WO | WO 98/55065 A1 | 12/1998 |
| WO | WO 99/01094 A1 | 1/1999 |
| WO | WO 99/01095 A1 | 1/1999 |
| WO | WO 00/00235 A1 | 1/2000 |
| WO | WO 2006/028612 A1 | 3/2006 |

OTHER PUBLICATIONS

"Antiperspirant Drug Products for Over-the-Counter Human Use: Final Monograph," Final Rule, Federal Register—Rules and Regulations, vol. 68, No. 110, Jun. 9, 2003, pp. 34273-34293.

Berner, G. et al. "Photoinitiators—An Overview", Journal of Radiation Curing, vol. 6, No. 2, Apr. 1979, pp. 2-9.

(56) References Cited

OTHER PUBLICATIONS

Lloyd, Jillian et al., "Female Genital Appearance: 'Normality' Unfolds," BJOG: An International Journal of Obstetrics and Gynecology, vol. 112, May 2005, pp. 643-646.

Mahdavi, Alborz et al., "A Biodegradable and Biocompatible Gecko-Inspired Tissue Adhesive," PNAS, vol. 105, No. 7, Feb. 19, 2008, pp. 2307-2312.

* cited by examiner

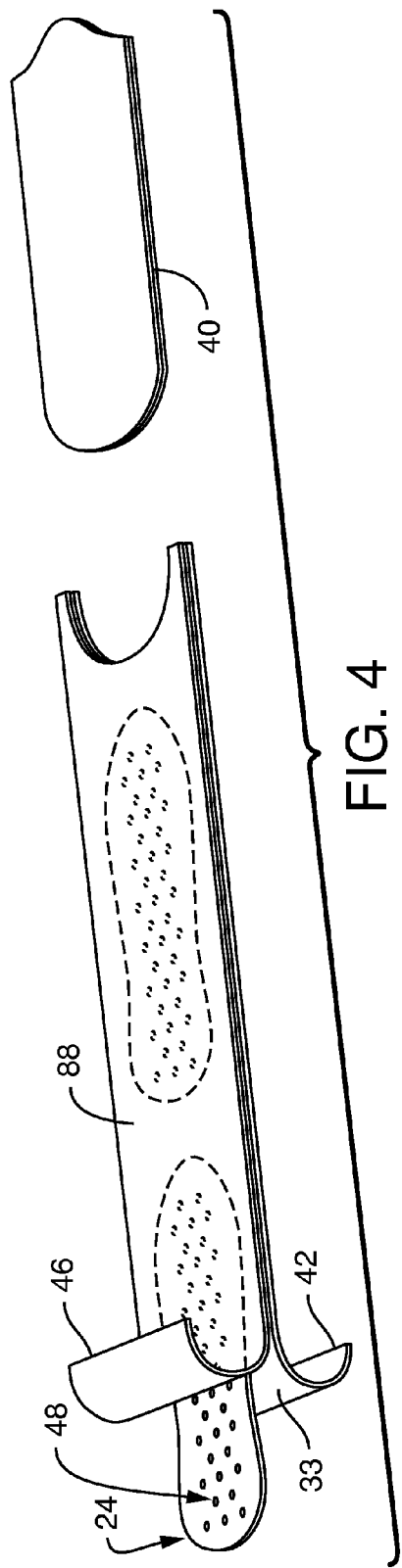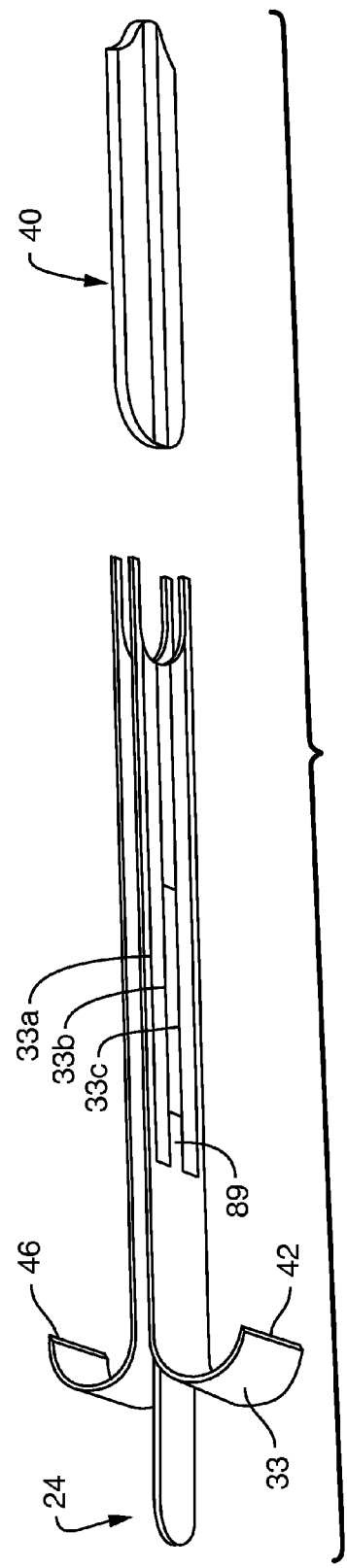

METHOD OF MANUFACTURING A BODY ADHERING ABSORBENT ARTICLE ORIENTATED IN THE MACHINE DIRECTION WITH REDUCED CURL

FIELD OF THE INVENTION

This disclosure relates to methods of making a body adhering absorbent article oriented in the machine direction, the article having little or no curl. Various methods of constructing individual body adhering absorbent articles are described that reduce or eliminate the amount of residual stretch present in the shell where components are attached.

BACKGROUND

Several methods have been proposed for making body adhering absorbent articles. The body adhering absorbent articles generally consist of components which are laminated to an elastic shell, which is generally in a tensioned state during the assembly process, to form a composite web of individual absorbent articles. When the discrete body adhering absorbent articles are die cut from the composite web the individual articles curl toward the elasticized shell material in the areas where it has been attached to the components as a result of residual stretch present in the shell material in the laminated regions.

Curling of a body adhering absorbent article is undesirable because it may interfere with peel strip removal, attachment to the body and the ability of the article to stay attached to the body. Curling of the product in the absorbent area may also interfere with the fit and gasketing of the product. Products which curl are also more difficult to convert, fold, and package increasing the level of defects, and machine downtime.

Accordingly there is a need for a method of manufacturing a body adhering absorbent article that reduces or eliminates the curl of the finished product, thereby enhancing customer satisfaction and easing manufacture.

SUMMARY

It has now been discovered that curl of body adhering absorbent articles may be reduced or eliminated by selectively reducing or eliminating the shell elastic tension in regions where components of the body adhering absorbent article, such as an adhesive transfer layer component or an absorbent article component, are to be attached to form the composite absorbent article web. Accordingly, in one aspect the present disclosure provides a method of manufacturing a body adhering absorbent oriented in the machine direction comprising supplying an elastic web of shell material having a longitudinal and transverse direction; stretching the web of shell material in the longitudinal direction; deadening at least one region of the stretched web of shell material in the longitudinal direction to form a longitudinal deadened zone; attaching at least one component to at least a portion of the longitudinal deadened zone to form a composite web material; and cutting the composite web material to form an absorbent article having a predetermined size and shape.

In still other aspects the present disclosure provides a method of manufacturing a body adhering absorbent oriented in the machine direction comprising supplying an elastic web of shell material having a longitudinal and transverse direction; maintaining the elastic web of shell material in an untensioned state; attaching at least one component to the untensioned elastic web of shell material to form a composite web material; and cutting the composite web material to form an absorbent article having a predetermined size and shape.

In yet other aspects the present disclosure provides a method of manufacturing a body adhering absorbent oriented in the machine direction comprising supplying an activatable web of shell material having a longitudinal and transverse direction; intermittently activating a portion of the web of shell material in the longitudinal direction to create activated and nonactivated portions of the web of shell material in the longitudinal direction; attaching at least one component to the at least one nonactivated portion of the web of shell material to form a composite web material; and cutting the composite web material to form an absorbent article having a predetermined size and shape.

In another aspect the present disclosure provides a method of manufacturing a body adhering absorbent oriented in the machine direction comprising supplying a web of shell material having elastic and nonelastic zones; attaching at least one component to the nonelastic zone of the web of shell material to form a composite web material; and cutting the composite web material to form an absorbent article having a predetermined size and shape.

In still another aspect the present disclosure provides a method of manufacturing a multi-segmented body adhering absorbent oriented in the machine direction comprising supplying a web of shell material; attaching an adhesive transfer layer to the web of shell material to form a first composite web; cutting the first composite web to form discrete panels; attaching an absorbent component to the discrete panels to form a second composite web; and cutting the second composite web material to form an absorbent article having a predetermined size and shape.

DESCRIPTION OF THE DRAWINGS

FIG. 4 shows a machine direction method of manufacturing an absorbent article component according to one embodiment of the present disclosure;

FIG. 5 shows a machine direction method of manufacturing an absorbent article according to one embodiment of the present disclosure;

DEFINITIONS

Figure 1:
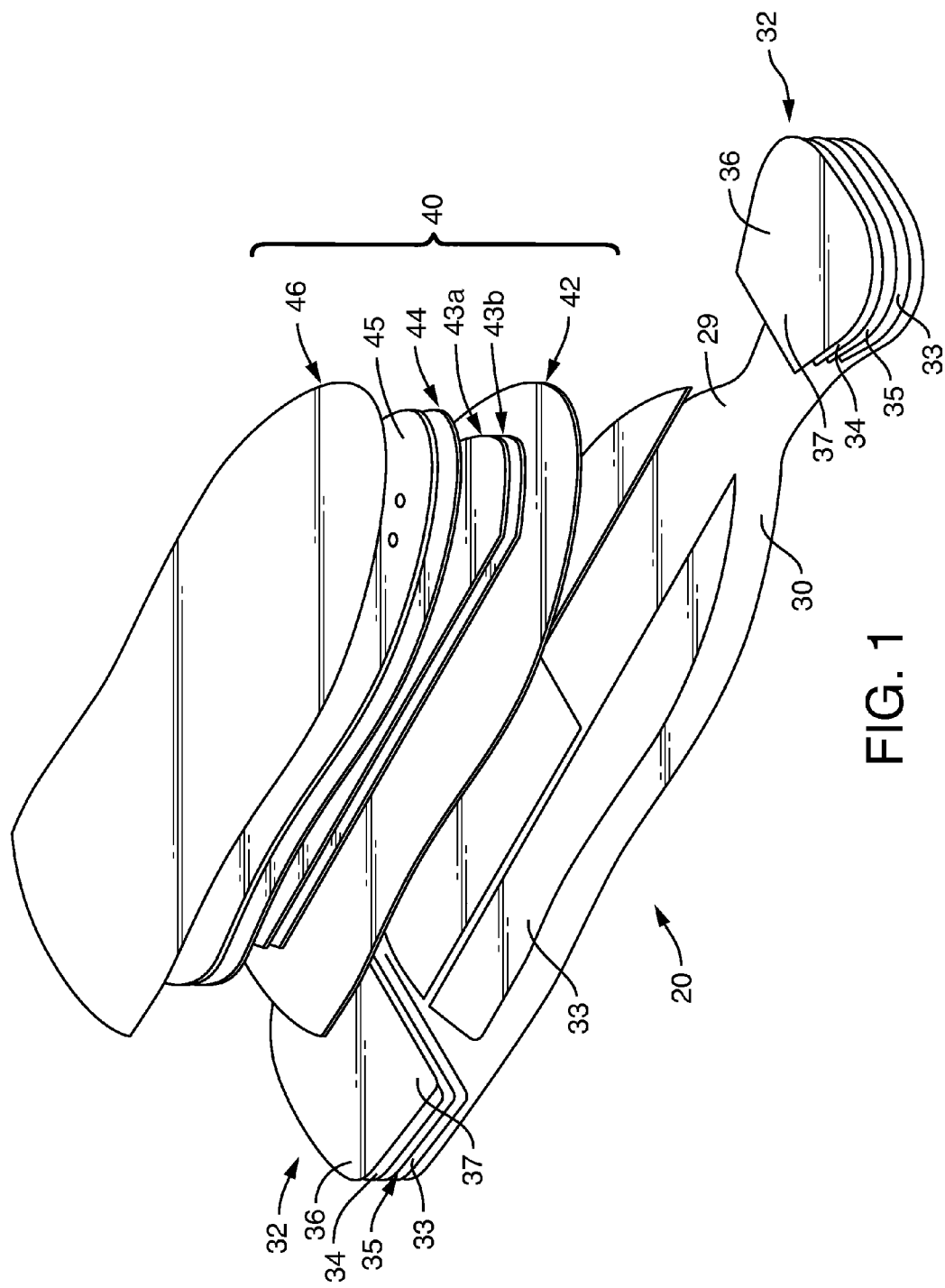
FIG. 1 is an exploded view of a body adhesive absorbent article according to one embodiment of the present disclosure.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

"Absorbent structure" refers to the central fluid handling portion of an absorbent article and may include but is not limited to one or more of the following components: cellulose fluff, superabsorbent material, coform, absorbent sponge material, surge material, or wicking material but does not include a topsheet or backsheet.

"Absorbent component" may include but is not limited to one or more of the following components: an absorbent structure, as defined above, a fluid pervious topsheet, a fluid impervious backsheet, or attachment adhesive.

As used herein, the term "adhesive transfer layer" generally refers to an adhesive region of the body adhering absorbent article that facilitates adhesion of the article to a user. In certain preferred embodiments the adhesive transfer layer comprises a lower peel strip, construction adhesive, a body attachment adhesive, a nonwoven carrier and an upper peel strip.

As used herein, the term "attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or a refastenable attachment. In addition, the attachment can be completed either during the manufacturing process or by the end wearer.

As used herein, "body-facing" means that surface or side of the article which is intended to be disposed toward or placed adjacent to the body of the wearer during ordinary use. The term "garment-facing" means that surface or side that is on the opposite side of the article from the body-facing surface or side. The garment-facing surface is an outward surface of the article and is intended to be disposed to face away from the wearer's body during ordinary use. The garment-facing surface is generally arranged to face toward or placed adjacent to the wearer's undergarments or clothing when the article is worn.

As used herein, the term "connected" is intended to mean directly connected and indirectly connected. By directly connected, it is intended that the connected elements are in contact with one another or affixed to one another. By indirectly connected, it is intended that one or more intervening or intermediate elements are between the two elements which are secured or "connected" together. The intervening elements may be affixed.

As used herein, the terms "elastomeric," "elastic," "elasticized," and "elastically" generally refer to that property of a material or composite by virtue of which it tends to recover its original size and shape after removal of a force causing a deformation. An elastomeric material is an extendable material having recovery properties. Suitably, an elastically extensible material can be elongated to at least 25% of its relaxed original length (percent elongation refers to the increase in the original length of the untensioned material, i.e., 0% refers to the original length of the untensioned material) in the direction of an applied biasing force, and which will recover, upon release of the applied force, at least 10% of its elongation. It is generally preferred that the elastomeric material or composite be capable of being elongated by from at least about 25% of its relaxed original length (i.e., an increase of 25% from its untensioned length) to about 200% of its relaxed original length, for example preferably from at least about 50 to about 100% of its relaxed original length.

As used herein, the phrase "orientated in the machine-machine direction" refers generally to the orientation of the manufactured absorbent article. For example, with reference to FIG. 7, where the longest dimension 98 of the absorbent article is orientated substantially parallel to the direction of travel 76 of the shell composite web 53, the absorbent article is said to be manufactured in the machine direction 76 and the absorbent article is said to be "orientated in the machine direction." Conversely, where the longest dimension of the absorbent article 98 is orientated substantially perpendicular to the direction of travel of the web 76, the absorbent article is said to be manufactured in the "cross-machine direction," or "CD."

"Untensioned" as used herein to describe a web of material does not mean lacking all tension. In order to handle and process moving webs, some moderate amount of tension is needed to hold the web or material in place. Accordingly, an "untensioned" web or material, as used herein, is under enough tension to process the material, but less than that required to cause substantial deformation (e.g., necking) of the material.

DETAILED DESCRIPTION

Generally, the present disclosure relates to methods of manufacturing a body adhering absorbent oriented in the machine direction wherein the resulting body adhering absorbent article has little or no curl. Various methods of constructing individual body adhering absorbent articles are described that reduce or eliminate the amount of residual stretch present in the shell where components, such as absorbent article components or the adhesive transfer layer components, are attached. Eliminating curl is important for facilitating use of the body adhering absorbent article, particularly in the region of the article that is adhered to the user. By eliminating curl both the fit and the function of the body adhering absorbent article may be improved.

Now with reference to FIG. 1, one embodiment of a body adhering absorbent article 20 is illustrated. Body adhering absorbent article 20 comprises a body adhering shell 29, and an absorbent component 40. The composition of the body adhering shell 29 may be varied depending upon the method of manufacturing. For example, as described in more detail below, where the method of manufacturing comprises deadening portions of the shell web material 30 or attaching components to the shell web material 30 while it is in an untensioned state, the shell material 30 may be a stretchable laminate of a woven or nonwoven fabric with a silicone polymer, wherein the silicone polymer has adhesive properties. In this aspect, the second side of the shell can be the woven or nonwoven fabric and the first side of the shell can be the silicone polymer. For example, in one embodiment the shell material 30 may be a stretchable laminate of a woven or nonwoven fabric such as the nonwoven composite containing an apertured elastic film disclosed in US Publication No. 2008/0095978, the contents of which are incorporated herein in a manner consistent with the present disclosure. Other suitable shell materials are discussed below.

Figure 2:
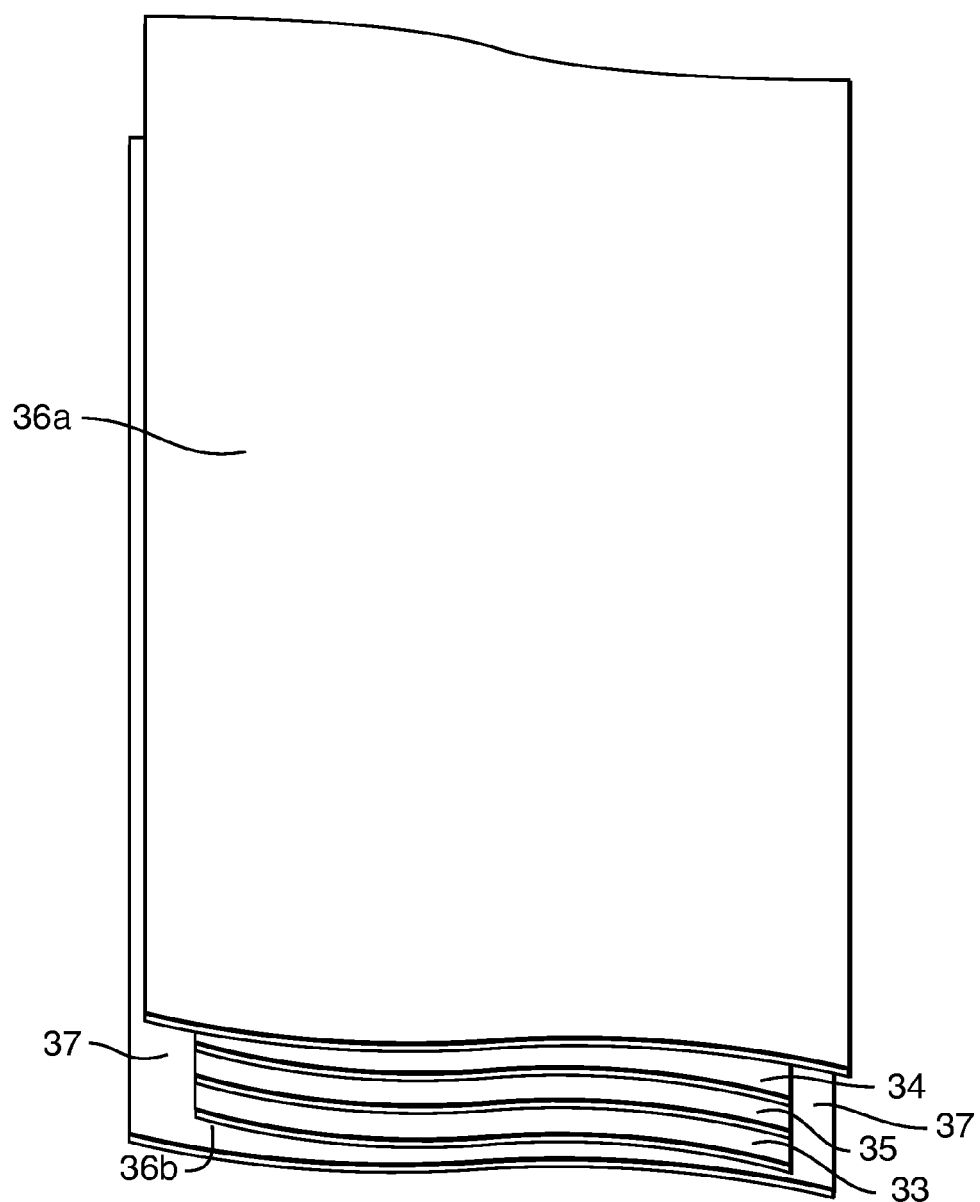
FIG. 2 is a cross sectional view of an adhesive transfer layer according to one embodiment of the present disclosure.
Figure 3:
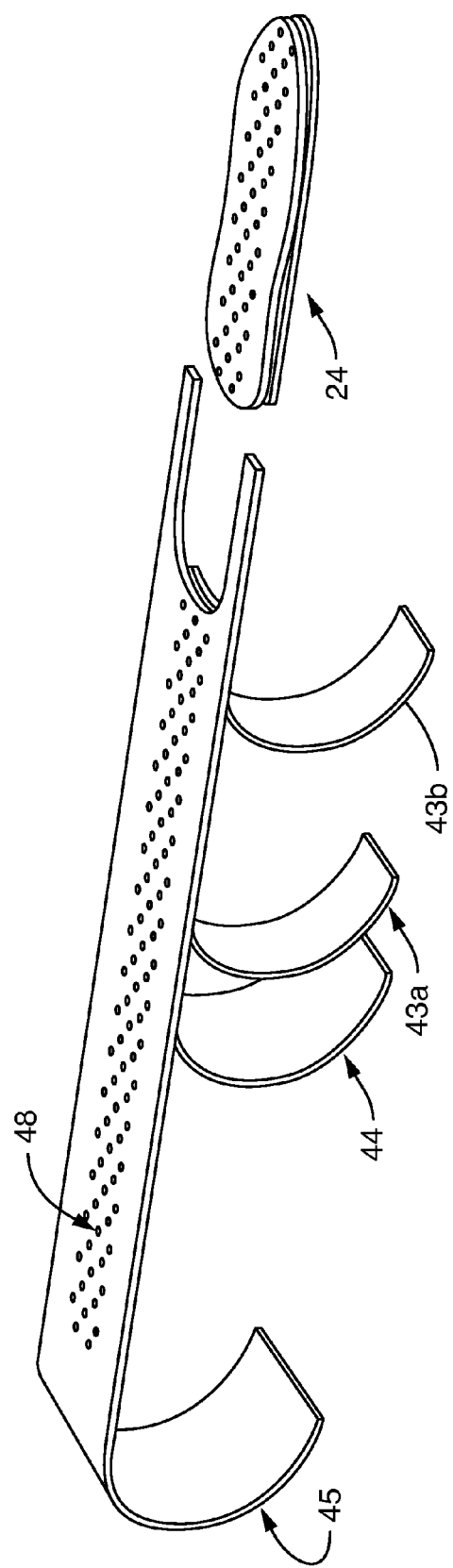
FIG. 3 shows a method of manufacturing an absorbent structure according to one embodiment of the present disclosure.

The body adhering shell 29 further comprises a body adhesive, for example an adhesive transfer layer (ATL) 32. A preferred configuration of the ATL 32 is shown in FIG. 2. In this embodiment the ATL 32 consists of lower peel strip 36b, construction adhesive 33, body attachment adhesive 34, nonwoven carrier 35, and upper peel strip 36a. The construction adhesive 33 may be, for example, Easymelt 34-5610 (Nation Starch Chemical Co., Bridgewater, N.J.), the body attachment adhesive 34 may be, for example, BMS gel 4a (Biomed Sciences, Inc., Allentown, Pa.), the nonwoven carrier 35 may be, for example, rayon/polyester Spunlace nonwoven (Biomed Sciences, Inc., Allentown, Pa.) and the peel strip 36 may be, for example, 24KSA final release paper (Tekkote Co., Leonia, N.J.).

In one embodiment an ATL 32 comprising a peel strip 36, body attachment adhesive 34, and nonwoven carrier 35 may be manufactured by providing a web of nonwoven carrier 35, providing a web of peel strip 36a, applying a body attachment adhesive 34 to the peel strip 36a and curing the adhesive 34, for example by treating the adhesive 34 with ultraviolet light. Once the adhesive 34 is cured to the appropriate level the peel strip adhesive composite is laminated to a nonwoven carrier 35. In a preferred embodiment the body attachment adhesive layer 34 is narrower than the peel strip 36a and may be narrower than the nonwoven carrier 35. This results in the formation of a user grasping section or finger tab 37 on the lateral side edges of ATL web 32. In a particularly preferred embodiment the ATL web 32 is made in a multi-wide configuration, slit into individual lanes and wound onto cores.

In another embodiment an ATL 32 comprising a lower peel strip 36b, construction adhesive 33, nonwoven carrier 35, body attachment adhesive 34, and upper peel strip 36a may be manufactured by providing a web of lower peel strip 36b, providing a web of nonwoven carrier 35, applying a construction adhesive 33 to the nonwoven carrier 35 and laminating the nonwoven carrier 35 and construction adhesive 33 to the lower peel strip 36b. A web of upper peel strip 36a is provided and a body attachment adhesive 34 is applied to upper peel strip 36a and cured to the appropriate level. The upper peel strip 36a with cured body attachment adhesive 34 is laminated to the nonwoven carrier 35, construction adhesive 33, and lower peel strip 36b laminate.

In still another embodiment an ATL 32 comprising a lower peel strip 36b, construction adhesive 33, nonwoven carrier 35, body attachment adhesive 34, and upper peel strip 36a may be manufactured by providing webs of lower peel strip 36b and nonwoven carrier 35 which are fed into the process, applying construction adhesive 33 to the nonwoven carrier 35 and laminating the nonwoven carrier 35 and construction adhesive 33 composite to the lower peel strip 36b. A web of upper peel strip 36a is provided and discrete patches of body attachment adhesive 34 are applied to upper peel strip 36a and cured. The upper peel strip 36a with cured discrete patches of body attachment adhesive 34 is laminated to the nonwoven carrier 35, construction adhesive 33, and lower peel strip 36b laminate. In this embodiment the discrete patches of body attachment adhesive layer result in the formation of lateral direction user grasping sections 37. ATL lower peel strip 36b and construction adhesive 33 may or may not be needed depending upon the method of making the body adhering absorbent article 20.

In another embodiment an ATL 32 comprising a lower peel strip 36b, construction adhesive 33, nonwoven carrier 35, body attachment adhesive 34, and upper peel strip 36a may be manufactured by providing webs of nonwoven carrier 35 and peel strip 36a which are fed into the process. The peel strip 36a is c-folded over onto itself forming user grasping section 37. Body attachment adhesive 34 is applied to the peel strip 36a, cured and laminated to the nonwoven carrier 35, construction adhesive, and lower peel strip 36b laminate.

In addition to the shell material 30 and ATL 32, the body adhering absorbent article 20 may comprise an absorbent component 40, which is generally attached to the first side of the shell material 30. The attachment may be in a permanent manner, meaning that the absorbent component 40 is generally intended not to be removable by the wearer of the article 20. Alternatively, the absorbent component 40 may be constructed to be removable by the wearer, meaning that the absorbent component 40 may be removed and replaced with another absorbent component 40 by the wearer of the article 20, or be replaced with nothing at all. In some aspects, when the absorbent component 40 is attached to the shell material 30 in a permanent manner, meaning that the absorbent component 40 is not intended to be removed by the wearer, various bonding means can be used, such as a construction adhesive for example. Examples of useable construction adhesives include any adhesive which will effectively hold the absorbent component 40 in place, so as not to be separated from the shell material 30. Commercially available construction adhesives usable in the present invention include, for example, Rextac™ adhesives available from Huntsman Polymers, Houston, Tex. Other means may be used to hold the absorbent component 40 to the shell material 30 including bonding techniques known in the art, including, but not limited to, adhesive bonds, cohesive bonds, thermal bonds, ultrasonic bonds, embossing, crimping, entangling, fusing, hook and loop, or the like, and combinations thereof.

Where the absorbent component 40 is preferably removably attached, the absorbent component 40 is held in place on the shell material 30 by a means which will allow the wearer to remove the absorbent component 40. One such means of holding the absorbent component 40 is by using a pressure sensitive adhesive. Suitable pressure sensitive adhesives include, but are not limited to, any commercially available pressure sensitive adhesive. Examples of suitable pressure sensitive adhesives usable to removably hold the absorbent article 40 in place on the shell material 30 include pressure sensitive adhesives available from National Starch, Bridgewater, N.J.

In certain embodiments it may be advantageous for the absorbent article 40 to have a backsheet 42 and more preferably a fluid impervious backsheet. The backsheet can serve to provide liquid impermeability for the absorbent component 40, such that any fluids entering the absorbent structure 24 will not flow through the structure to the clothing of a wearer. One example of a commercially available fluid impervious backsheet is the XP-3473a baffle available from Huntsman Packaging Corporation, Houston, Tex.

The absorbent structure may comprise wicking layers 43a and 43b, which may be formed from meltblown microfiber such as the 50 gsm meltblown fibers commercially available from Yuhan-Kimberly Ltd., Korea. The absorbent structure 24 may further comprise an absorbent layer 44, intake layer 45 and topsheet 46. The absorbent layer 44 may contain one or more layers of absorbent materials, such as fibrous materials and/or superabsorbent materials for example. Each of the layers can contain similar materials or different materials. Materials that can be used to form the absorbent layer 44 include those materials conventionally used in absorbent articles and includes materials, such as, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency.

In a preferred embodiment the body adhering absorbent article 20 comprises a peel strip 36, which extends in the longitudinal direction (machine direction) 76 beyond the extent of the body attachment adhesive 34 forming a user grasping section also know as a finger tab 37. The presence of finger tab 37 allows the user to grasp the peel strip by placing their thumb under the unattached peel strip region and grasping the peel strip in the user grasping section 37 between the thumb and forefinger. The user of the product applies a peeling force to remove the anterior and posterior peel strips 36.

Figure 6:
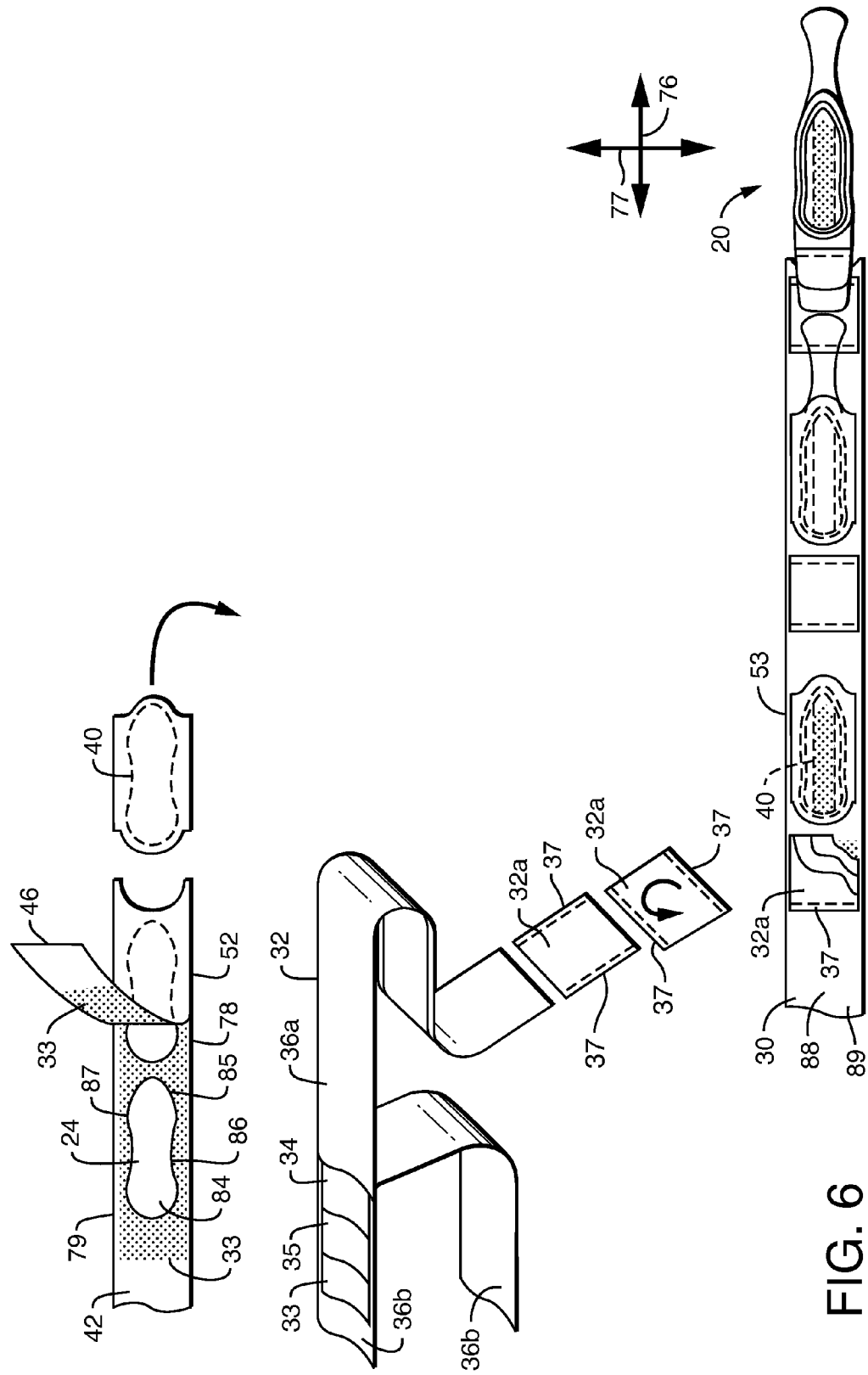
FIG. 6 shows a machine direction method of manufacturing a body adhering absorbent article according to another embodiment of the present disclosure.

Referring to FIG. 6, one method of manufacturing a body adhering absorbent article oriented in the machine direction is illustrated. The process has a machine direction 76 and a cross-machine direction 77. The process is initiated by providing a fluid permeable body facing web 46 also known as a topsheet, or body-side liner. Topsheet 46 should be able to manage different body excretions depending on the type of product. In feminine care products, often the body-side liner or topsheet 46 must be able to handle menses and urine. In certain embodiments the topsheet 46 may include a layer constructed of any operative material, and may be a composite material. For example, the body-side liner or body-contacting layer can include a woven fabric, a nonwoven fabric, a polymer film, a film-nonwoven fabric laminate or the like, as well as combinations thereof. Topsheet web 46 has a left side 78 and a right side 79. A construction adhesive 33 is applied to topsheet web 46. Suitable construction adhesives include, for example, Rextac™ adhesives, as well as adhesives available from Bostik Findley, Inc, Wauwatosa, Wis.

After application of the construction adhesive 33 absorbent structures 24 are applied to web 46. Absorbent structures 24 may contain one or more layers of absorbent materials, such as fibrous materials and/or superabsorbent materials for example. That is, absorbent structures 24 may be a single layer of absorbent materials or may be a multilayer structure. Each of the layers can contain similar materials or different materials. Absorbent structures 24 are further defined as having an anterior portion 84 and a posterior portion 85. Anterior portion 84 is designed to align with the anterior of the wearer in use and posterior portion 85 is designed to align with the posterior of the wearer in use. Absorbent structures 24 also have a left side 86 and a right side 87. In this embodiment there is one longitudinal series of absorbent structures 24 that are positioned on topsheet web 46. This longitudinal series is positioned such that left side 86 of absorbent structures 24 is adjacent to the left side 78 of topsheet web 20. This longitudinal series of absorbents structures 24 follow a sequence where the posterior portions 85 of each absorbent structure 24 in the series are adjacent to the anterior portion 84 of the subsequent absorbent structures 24.

After the application of the absorbent structures 24, a fluid impermeable backsheet web 42 is delivered. Alternately backsheet web 34 can be a fluid pervious web. Backsheet web 42 may, for example, include a polymeric film, a woven fabric, a nonwoven fabric or the like, as well as combinations or composites thereof. For example, the backsheet may include a polymer film laminated to a woven or nonwoven fabric. In a particular feature, the polymer film can be composed of polyethylene, polypropylene, polyester or the like, as well as combinations thereof. Construction adhesive 33 is applied to backsheet web 42 and the topsheet 46, absorbent structures 24, and backsheet 42 are laminated together to form a composite web 52. The composite web 52 may then be cut to form individual absorbent article components 40. In a preferred embodiment construction adhesive is applied to the backsheet web prior to cutting into individual absorbent articles 40. As shown in greater detail in FIGS. 4 and 5 pressure sensitive adhesive or construction adhesive 33 is applied to the garment facing side 89 of backsheet 42. In a particular embodiment pressure sensitive adhesive is applied in three lanes where the outboard lanes 33a and 33c are continuous and the center lane 33b is discontinuous.

With further reference to FIG. 6, manufacture of the body adhering absorbent article 20 continues with delivery of the web of a shell material 30 having a body facing side 88 and a garment facing side 89. As noted previously the shell material 30 can include a polymeric film, a woven fabric, a nonwoven fabric, a foam or the like, as well as combinations or composites thereof. In some aspects, shell material may include a laminate structure, such as a polymer film laminated to a woven or nonwoven fabric. The exact composition of the shell material 30 may vary depending on the method of manufacture, as described more fully below. In certain embodiments the shell web 30 is corona treated to improve its adhesion properties. Alternately shell material 30 can be pre-corona treated. A web of pre-laminated composite 32 referred to as an "Adhesive Transfer Layer" or ATL comprising a carrier sheet 35, body adhesive 34, and peel strip 36 is provided and adhered to the web of shell material 30 to form a shell composite web 53. In a particular embodiment shown in FIG. 6 ATL web 32 is segmented into discrete ATL patches 32a. Patches 32a are then rotated 90 degrees to properly align the finger tab 37 so that it is perpendicular to the machine direction 76.

Manufacture continues with the preparation of the shell composite web 53 for attachment of absorbent article components 40. An initial die cut is made in composite web 52 to remove a portion of material that will be covered by absorbent article 40. In an alternate embodiment, as illustrated in FIG. 6, die cutting can be eliminated if absorbent article components 40 are positioned within or are coextensive with individual body adhering shell 29. An attachment means, such as an adhesive 33, is then applied to the shell composite web 53. In other embodiments the attachment means may be applied to the composite absorbent web 52 as illustrated in FIGS. 4 and 5. Attachment means can be eliminated if the absorbent component 40 has an attachment means for attaching it to body adhering shell 29. Alternately the attachment means can be a one part system, e.g. construction adhesive 33 for attaching absorbent article 40 to body adhering shell 29. Alternately attachment means can be a two part attachment system, not shown, such as a hook and loop fastener, cohesive, snaps, buttons, etc. where one part of the two part attachment means is located on body adhering shell 29 and the second part of attachment means 21 is located on absorbent component 40.

Next individual absorbent article components 40 are delivered and attached to body facing surface 88 of shell composite web 53 such that barrier layer 42 of absorbent component 40 is adjacent to body facing surface 88 of composite web 53. In this embodiment construction adhesive 33 is used to make the attachment. One skilled in the art however, will appreciate that "attach" refers to any method of joining, adhering, connecting, bonding, sewing together, or the like, of two elements. Two elements will be considered to be attached together when they are integral with one another or attached directly to one another or indirectly to one another, such as when each is directly attached to intermediate elements and include permanent, releasable, or a refastenable attachment. Manufacture continues by die cutting individual body adhering absorbent articles 20.

Figure 14:
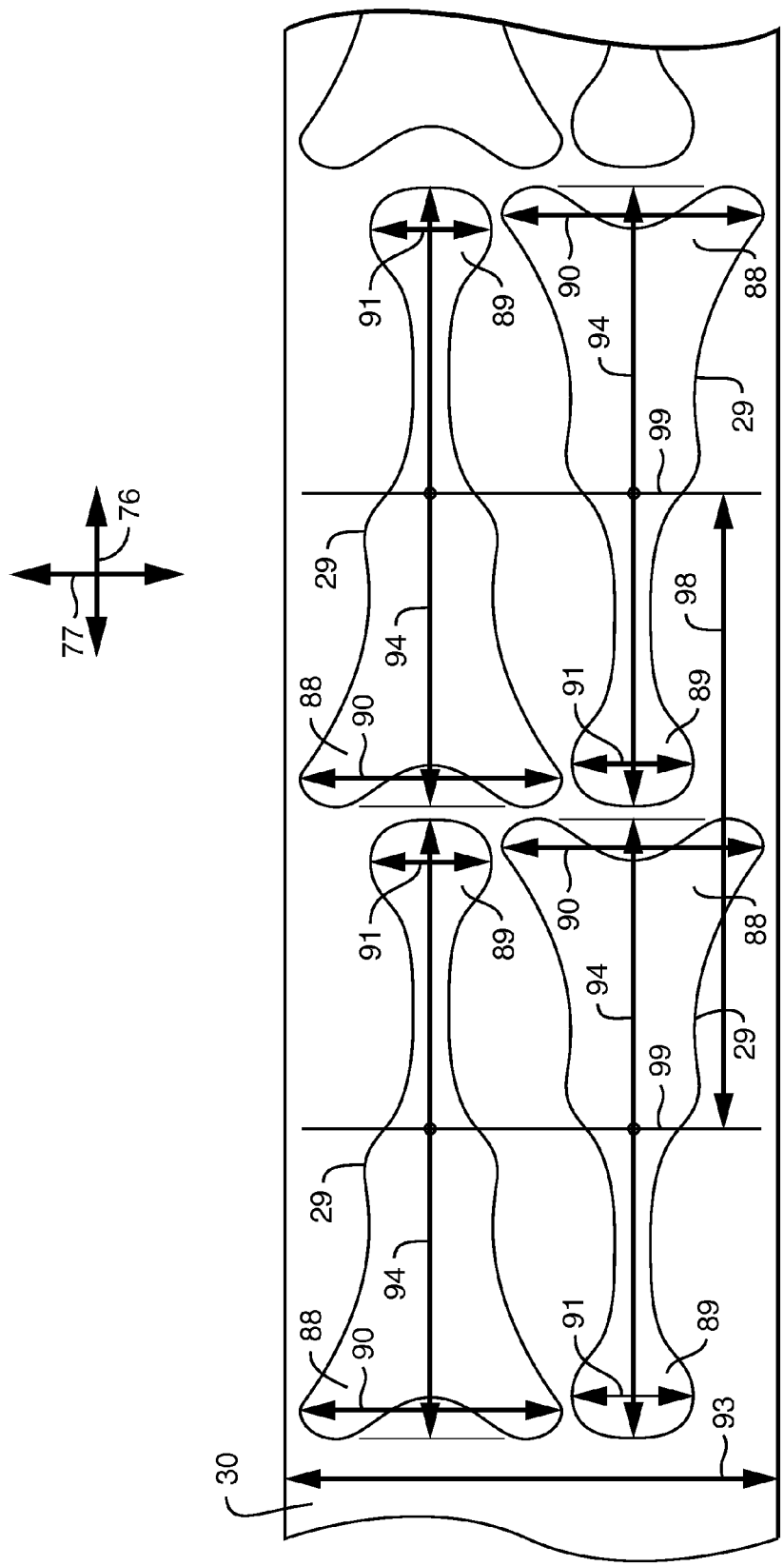
FIG. 14 shows one embodiment for manufacturing a machine direction oriented body adhesive absorbent article in a multi-lane nested configuration.

In an alternate embodiment, shown in FIG. 14, a multi-lane process can be employed to produce more than one series of machine directional oriented body adhering absorbent articles 20. In a particularly preferred embodiment the body adhering absorbent articles may be manufactured in a nested pattern to reduce the amount of raw material necessary to make an article. For example, as illustrated in FIG. 14, the amount of shell web material necessary to make one product is equal to 0.5 multiplied by the dimension 93 multiplied by the dimension 98 where the dimension 93 is the width of shell web 30, dimension 90 is the widest width of the anterior portion 88 of shell 29, dimension 91 is the widest width of the posterior portion 89 of shell 29, dimension 94 is the length of shell 29 and passes through the midpoints of lines 90 and 91 and dimension 98 is the length between lines 99 where lines 99 pass through the midpoints of lines 94. In the illustrated embodiment the dimension 93 is equal to about 193 mm and dimension 98 is equal to about 252 mm. The amount of shell material necessary to make one shell 29 in this example is 24,318 mm². This represents a 41% reduction of shell material as compared to a non-nested configuration.

Figure 8:
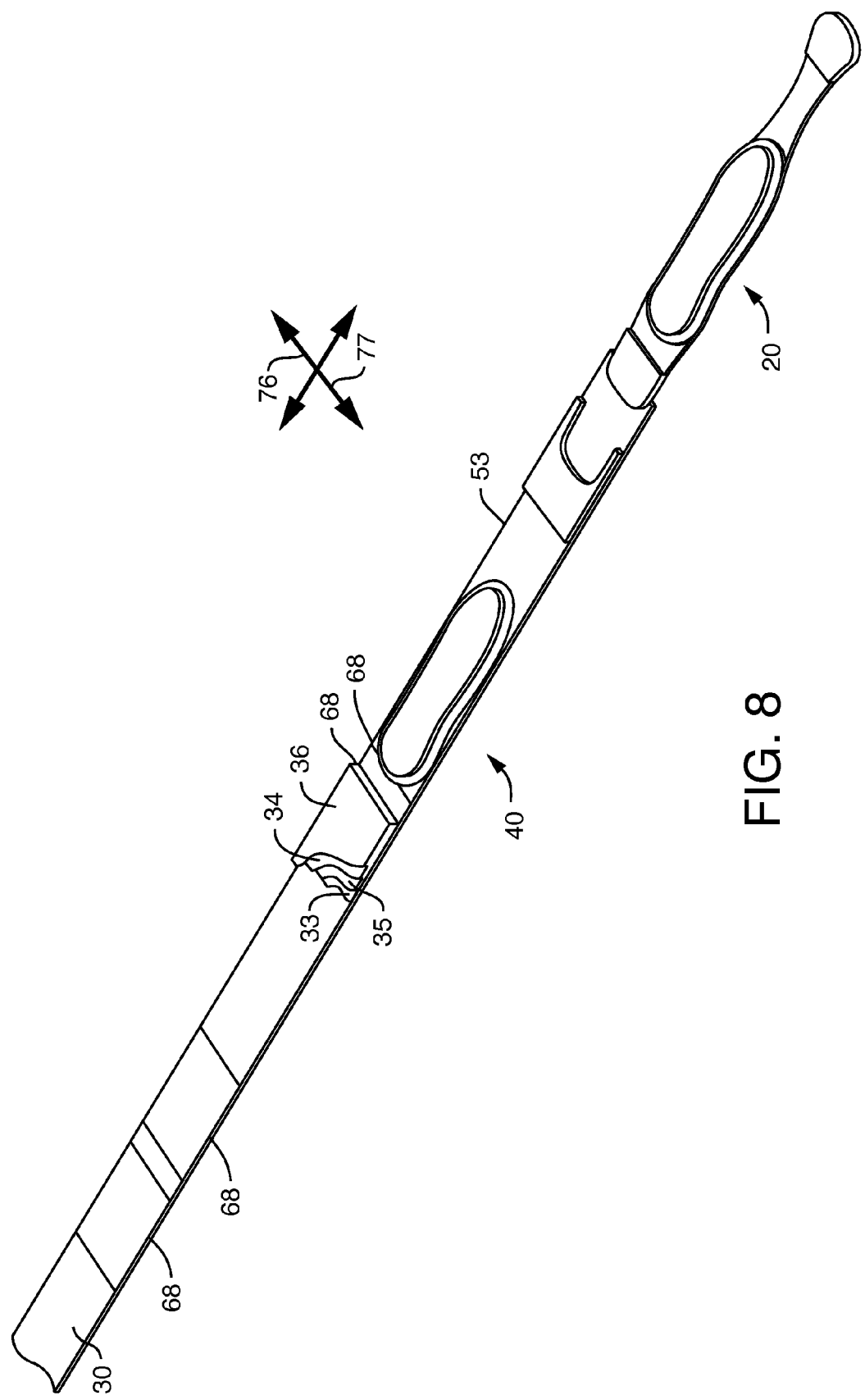
FIG. 8 shows a machine direction method of manufacturing a body adhering absorbent article according to another embodiment of the present disclosure.

Now with reference to FIG. 8, one method of making a body adhering absorbent article 20 having reduced curl is illustrated. In this embodiment a web of shell material 30 is initially introduced in an unstretched, nonactivated or untensioned state. The web of shell material is then stretched and the remainder of the manufacturing process is carried out with the material in a tensioned state.

Preferably the web material 30 is a nonwoven web of fibrous material such as, for example, a spunbond web, a meltblown web, bonded carded web, or a combination thereof. The material may be made of an elastomeric fiber forming polymer. A meltblown web used in this invention may initially be produced using conventional meltblowing processes and apparatus as known in the art whereby a cohesive web is formed. A nonwoven composite web used in this invention may initially be formed by techniques also well known in the art and described in US Publication No. 2008/0095978.

The shell material 30 may be stretched and maintained under tension using methods known in the art. For example, the shell web may be initially introduced in an untensioned state, for example by unwinding the web onto a conveyor and more preferably a vacuum conveyor. The rate of the feed roll may be adjusted to maintain the web in an untensioned state as it is advanced along the conveyor. The conveyor transports the untensioned web to a rotating drum that is driven at a higher rate of speed than the incoming web. The speed differential results in the web being stretched into a tensioned state as it is transferred to and carried about the circumference of the drum. In one preferred embodiment, the drum is a vacuum drum. After about 220° of travel around the drum the web is transferred to a second vacuum conveyor, which transports the web along the process. Preferably the speeds of the conveyor and the drum are synchronized such that the web is maintained in a tensioned state. In other embodiments the web may be maintained in a tensioned state adjusting the unwind speed relative to the speed of the vacuum conveyor such that the web is maintained under tension.

After the web is stretched, portions 68 of the web 30 are deadened. Deadening refers to the process by which the extension, retraction or elastic properties of a web are reduced or eliminated by, for example, bonding, the application of heat, adhesive or a patch of inelastic material. Bonding means may include, but are not limited to pressure bonding, ultrasonic bonding, adhesive bonding, thermal bonding, or the like. In a particularly preferred embodiment regions 68 are deadened by forming bond lines in one or more selected regions of the stretchable nonwoven web or laminate material in one or more selected directions, whereby the stretchability in the selected direction of the material can be controlled and substantially reduced in the region(s) of the bond lines. For example, a material with an initial stretch of from about 100 to about 200% in the machine direction can be reduced to about 0 to about 10% stretch with bond lines that cover from about 80 to about 100% of the material width. By applying bond lines to the shell material 30, an elastic nonwoven web or laminate material having zoned stretching may be produced. For example, by applying bond lines in a direction parallel to the cross-machine direction, deadened regions of material 68 are produced, such that when a tensioning force is applied in the machine direction the deadened regions 68 will not stretch or exhibit reduced stretching. The stretchability of the material is easily controlled during the bond line application process, by varying the length, thickness and density or frequency of the bond lines.

Once regions 68 have been deadened, components such as an ATL component 32 or an absorbent component 40 are attached to the deadened regions 68 of the shell web 30. The components may be attached using any method known in the art, for example, pressure bonding, adhesive bonding, thermal bonding and ultrasonic welding. Once the components are attached to form a composite web 53, individual body adhering absorbent articles 20 are die cut from the composite web 53. Upon cutting, the shell material is untensioned, however, the deadened laminated areas 68 will have little or no residual tension thus reducing or eliminating the curl in the relaxed untensioned body adhering absorbent article 20.

Figure 7:
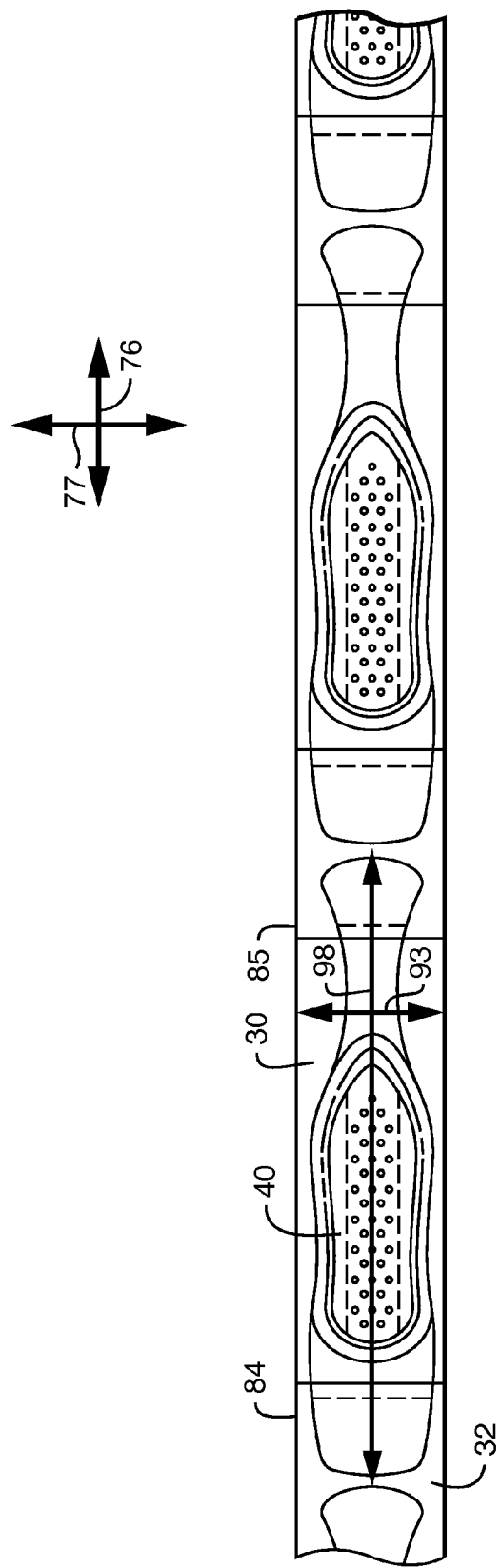
FIG. 7 is a top view of a web of body adhering absorbent articles according to still another embodiment of the present disclosure.
Figure 9:
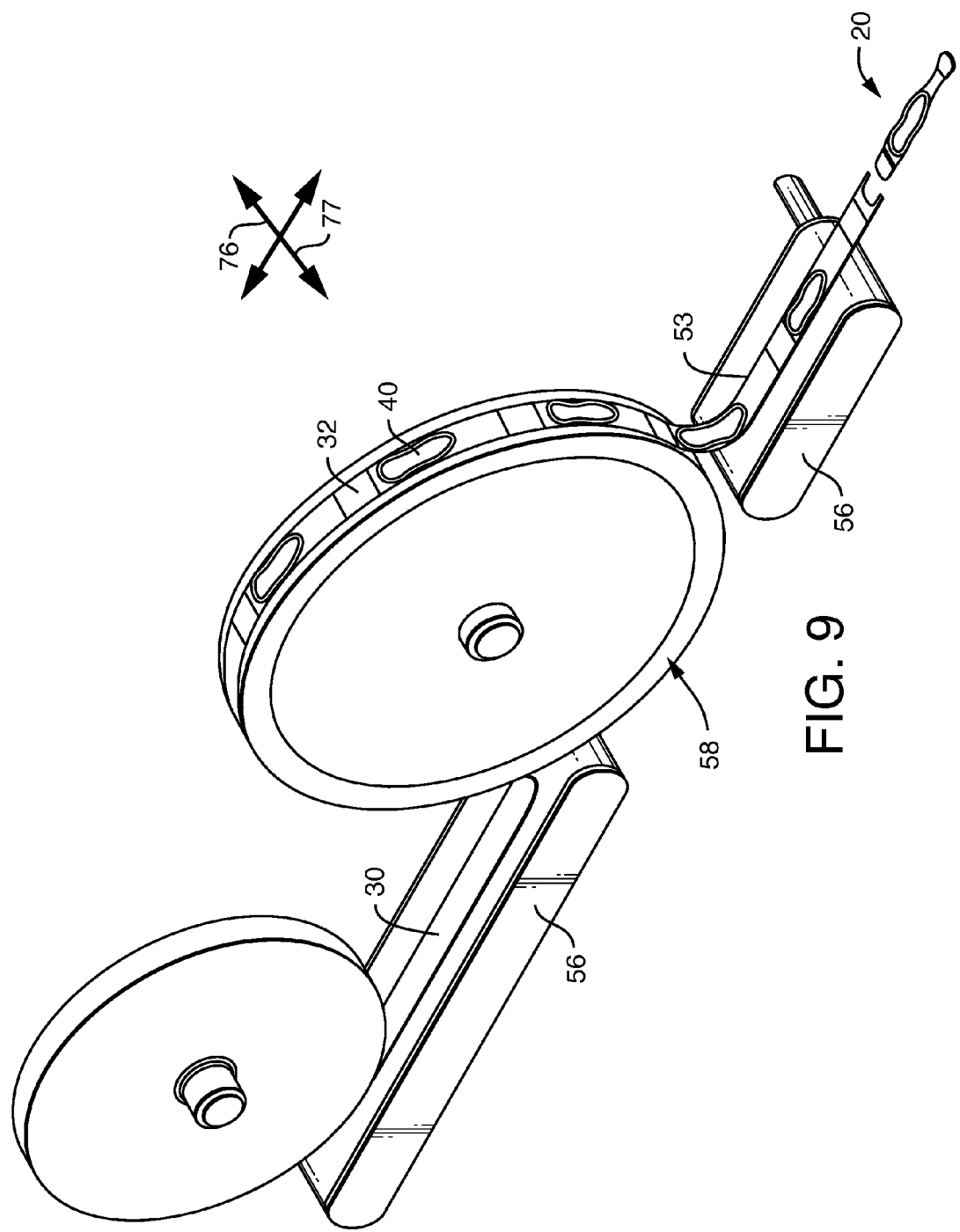
FIG. 9 shows a machine direction method of manufacturing a body adhering absorbent article according to still another embodiment of the present disclosure.

Turning now to FIG. 9, another embodiment for manufacturing a body adhesive absorbent article 20 is illustrated. As shown in FIG. 7 the shell web 30, which is preferably an elastic nonwoven composite containing an apertured elastic film such as that described in US Publication No. 2008/0095978, is initially introduced in an untensioned state. In one embodiment the shell web 30 is introduced in an untensioned state by unwinding the web unto a conveyor 56 and more preferably a vacuum conveyor that is synchronized with the web feed roll to maintain the shell web 30 in an untensioned state. The shell web 30 is carried along the conveyor 56 and transferred to a drum 58, which like the feed roll, is synchronized with the conveyor 56 to maintain the web in an untensioned state. In a preferred embodiment, the drum 58 is a vacuum drum. A drive means (not shown) for the drum 58 rotates it in a clockwise direction. Alternatively, the web may be carried along a first conveyor and transferred to a second conveyor having a vacuum for retaining the web in an untensioned state. Preferably the second conveyor, like the feed roll, is synchronized with the first conveyor to maintain the web in an untensioned state.

While the shell web 30 is maintained on the drum 58 in an untensioned state, components such as an ATL component 32 and an absorbent component 40 are attached to the untensioned shell web 30. The components may be attached using any method known in the art, for example, adhesive bonding, pressure bonding, thermal bonding and ultrasonic welding.

After about 220° of travel around drum 58 a second conveyor 56 synchronized with the drum 58 to maintain the shell web 30 in an untensioned state removes the shell composite web 53 from the drum 58 and transports it along the process. In a particular embodiment, after the components 32 and 40 have been attached to the shell web 30 the composite web 53 is transferred to a vacuum conveyor 56 to maintain the shell composite web 53 in an untensioned state. The untensioned shell composite web 53 may then be die cut to form individual body adhering absorbent articles 20. When the individual body adhering absorbent articles 20 are die cut from the shell composite web 53 little or no curl will be present as a result of little or no residual tension in the shell laminated regions.

Figure 10:
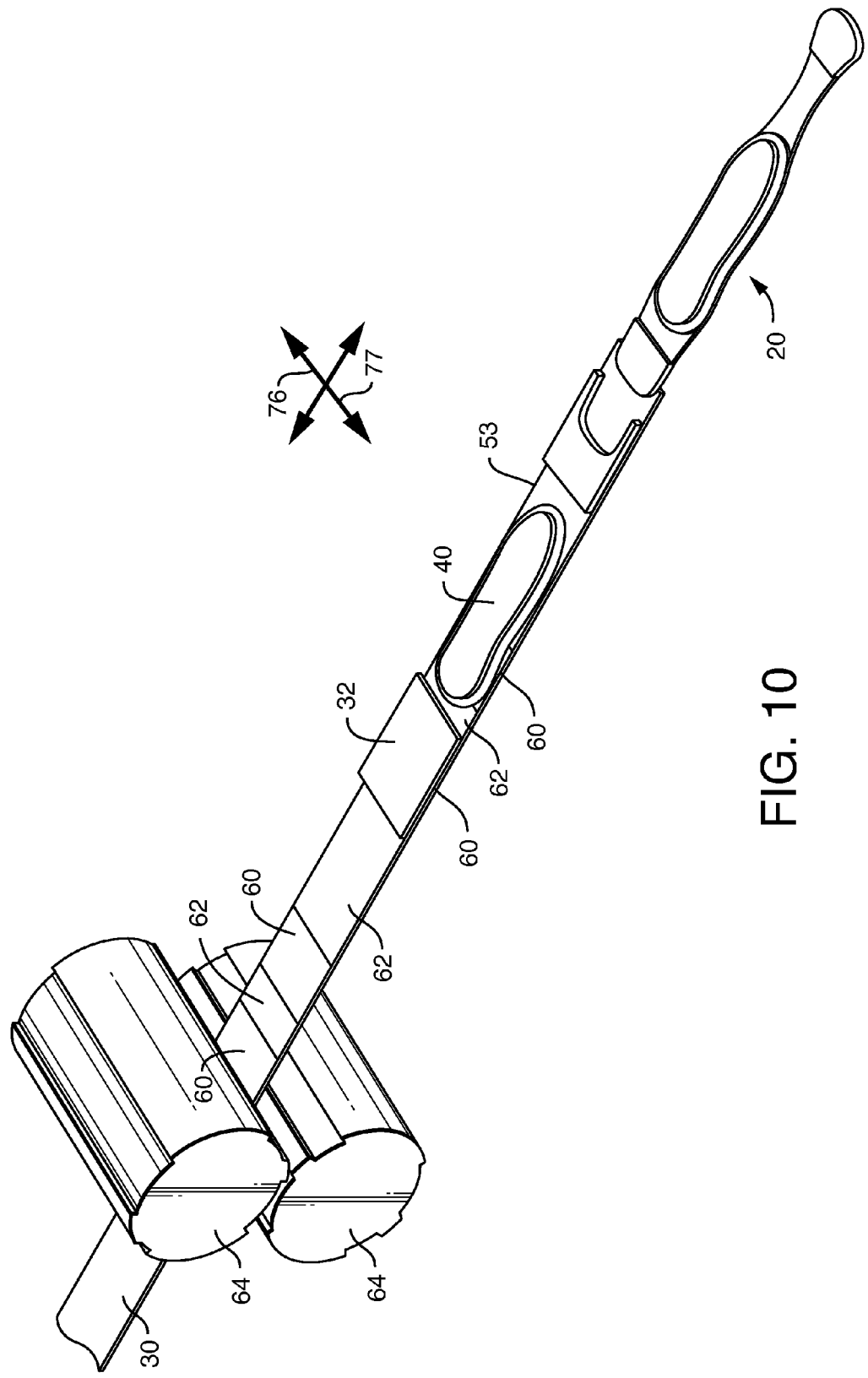
FIG. 10 shows a machine direction method of manufacturing a body adhering absorbent article according to another embodiment of the present disclosure.

With reference to FIG. 10, another embodiment for manufacturing a body adhering absorbent article 20 is illustrated. As shown in FIG. 10, a web of shell material 30 is mechanically activated by mechanically treating one or more selected regions 62 of the shell web 30 in one or more selected directions, whereby the stretchability in the selected direction of the material can be controlled and substantially increased in the region(s) mechanical treatment. For example, the elasticity of a material with an initial stretch of from about 0 to about 25% in the machine direction can be increased to about 50 to about 200% stretch with machine treatment that is orientated in the cross-machine direction and treats from about 80 to about 100% of the material width. By mechanically treating the shell material 30 an elastic web material having zoned stretching in the machine direction 76 may be produced. For example, by mechanically treating the web in a direction parallel to the cross-machine direction, treated regions or zones of material 62 are produced, such that when a tensioning force is applied in the machine direction the treated zones 62 will stretch or exhibit increased stretching, while unmachined, untreated zones 60 display little or no additional stretch.

Accordingly, a web having mechanically activated and nonactivated zones may be prepared as described in U.S. Pat. Nos. 4,834,741 and 5,366,782, the contents of which are incorporated herein in a manner consistent with the present disclosure. For example a web, such as a polyolefin apertured web or a low density polyethylene film, both of which are substantially inelastic, is longitudinally passed through rolls 64 of ring-rolling apparatus illustrated in FIG. 10 to make web having activated and nonactivated zones. Rolls 64 consist of teeth which are separated by a uniform distance, p, more commonly known as pitch. The teeth of each roll 64 are offset by a distance P/2 from each other. The distance between the outer circumferences of the rolls 64 can be varied by an intermeshing distance, E, more commonly known as the engagement. In other embodiments the web may be an elastic web, such as an elastic web formed from KRATON® D SIS (Kraton Polymers USA) that has been laminated to inelastic nonwoven carrier webs such as spunbond.

Ring-rolling of the shell web 30 incrementally stretches and thereby plastically deforms a plurality of the beam-like elements in the transverse direction. The stretching of the beam-like elements occurs incrementally across the width of the web (transverse direction) as the film is constrained at the tips of the teeth and is stretched an amount that is proportional to the pitch and the engagement. As the engagement depth of the rolls 64 is increased, the incremental stretching and the plastic deformation of the inelastic nonwoven facings are increased.

Once activated 62 and nonactivated 60 regions have been formed, components such as an ATL component 32 or an absorbent article component 40 are attached to the nonactivated regions 60 of the web. The components may be attached using any method known in the art, for example, adhesive bonding, pressure bonding, thermal bonding and ultrasonic welding. Once the components are attached to form a composite web 53, individual body adhering absorbent articles 20 are die cut from the composite web 53. As a result of this configuration the components are laminated to nonactivated, non-stretchable portions of the web so that when the individual body adhering absorbent articles 20 are die cut from the composite web 53 there will be little or no residual stretch in the shells laminated regions where the ATL component 32 or absorbent component 40 are attached, thereby reducing or eliminating curl in the individual body adhering absorbent article 20.

Figure 11:
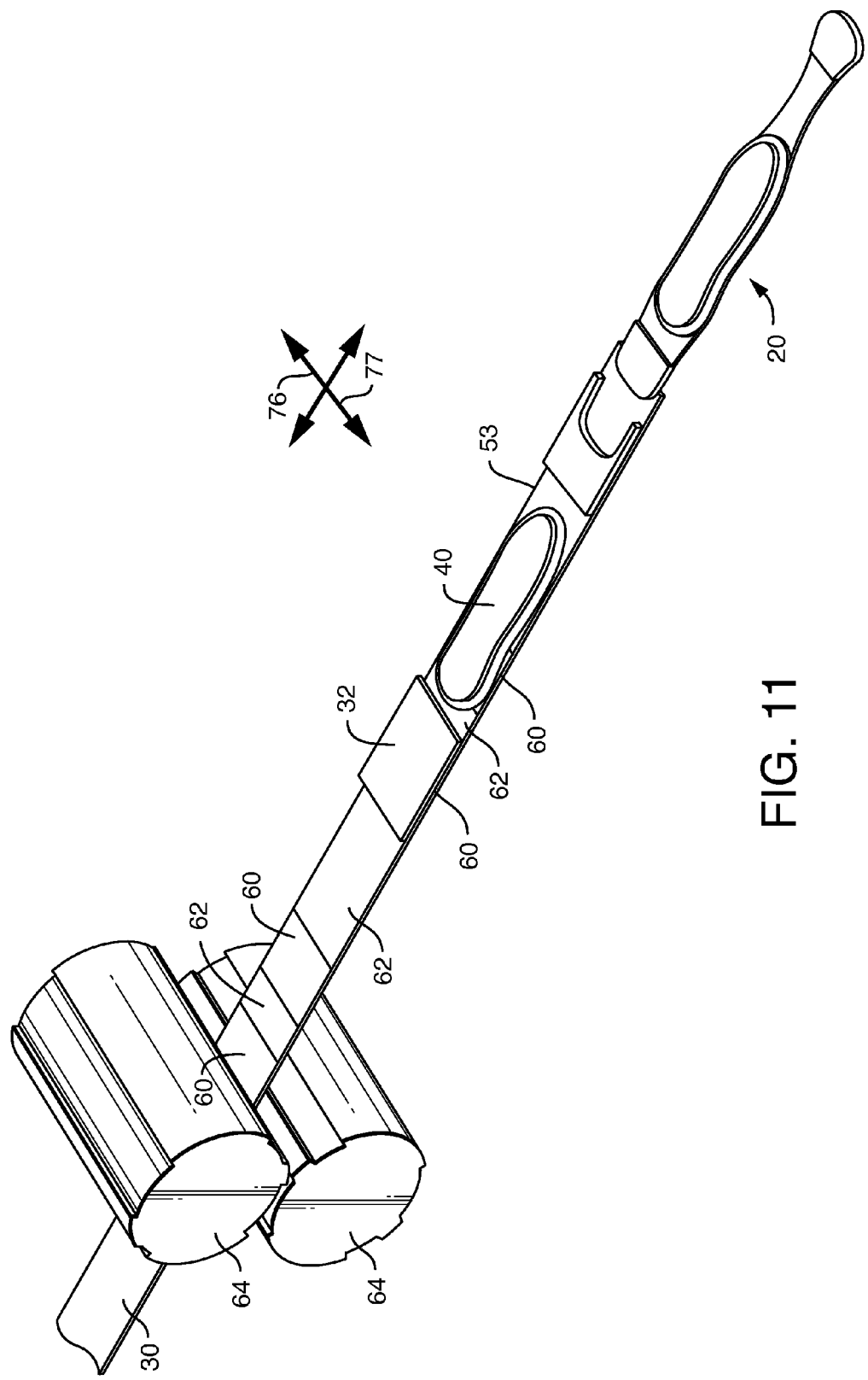
FIG. 11 shows a machine direction method of manufacturing a body adhering absorbent article according to yet another embodiment of the present disclosure.

Turning now to FIG. 11 another embodiment for manufacturing a body adhering absorbent article 20 is illustrated. As shown in FIG. 11, a web 30 is activated by treating one or more selected regions 62 of the web 30 in one or more selected directions, whereby the stretchability in the selected direction of the material can be controlled and substantially increased in the selectively treated region(s). For example, the elasticity of a material with an initial stretch of from about 0 to about 25% in the machine direction can be increased to about 100 to about 200% stretch with selective treatment that is orientated in the cross-machine direction and treats from about 80 to about 100% of the material width. By selectively treating the shell material 30 in the cross-machine direction, an elastic web material having zoned stretching in the machine direction may be produced. For example, by thermally treating the web in a direction parallel to the cross-machine direction, treated regions or zones of material 62 are produce, such that when a tensioning force is applied in the machine direction the treated zones 62 will stretch or exhibit increased stretching, while untreated zones 60 display little or no additional stretch.

Accordingly, in one embodiment the web of shell material may comprise a latent elastic laminate that upon activation may suitably be stretched by at least about 25%, or at least about 100%, or at least about 200%, and may suitably recover at least about 5%, or at least about 15%, or about 25% of the stretched length. The latent elastic laminate materials may have a basis weight between about 2 and about 60 grams per square meter (gsm), or between about 5 and about 30 gsm, or between about 5 and about 15 gsm. Suitable latent elastic materials include, for example, the latent elastic laminate described in U.S. Pat. No. 7,820,001, the contents of which are incorporated herein in a manner consistent with the present disclosure. In a preferred embodiment the latent elastic laminate is formed as a multi-segmented film web having heat activatable regions or zones where one or more of the segments within the multi-segmented film comprises an elastic segment, any additional layers laminated thereto desirably comprise an extensible material or fabric. In this regard, the additional layer or layers can comprise, as examples, extensible nonwoven materials (e.g., creped nonwovens or non-wovens comprising highly crimped fibers), meshed fabrics, loosely woven fabrics, elastic composite materials and/or other like materials. Desirably the fabric comprises one or more layers of thermoplastic fibers which are elastic, inherently extensible or which have been treated so as to become extensible and/or elastic and which also have a cloth-like hand and drape. The composition of the thermoplastic polymer may be selected as desired to achieve a material having the desired physical attributes such as, for example, elasticity, hand, tensile strength, cost and so forth. Further, the outer nonwoven layer may be treated such as, for example, by embossing, hydroentangling, mechanically softening, printing, anti-static treatment or treated in some other manner in order to achieve desired aesthetics and/or functional characteristics.

In one embodiment, to activate the latent elastic laminate, the laminate is heated to at least a softening point of the latent polymer. When the latent polymer softens, the elastic members are able to retract and gather the substrate, thereby resulting in a gathered structure that is elastic. Latent heat activation may be achieved at temperatures between about 70 and about 290° C., or between about 70 and about 200° C., depending largely upon the glass transition temperature of the latent polymer as well as the basis weight of the polymer and the laminate, and also depends upon the dwell time. For example, the latent heat activation may be achieved at a temperature between about 140 and about 160° C. with a dwell time of about 5 to about 10 seconds, or at a temperature between about 70 and about 160° C. with a dwell time of about 1 to about 10 seconds.

Accordingly, in one embodiment a transfer roller feeds the web 30 having heat activatable elastic zones into a heat activation unit. The heat activation unit may comprise, for example, a pair of rolls (two shown in FIGS. 11, 66 and 66). The rolls are preferably configured to provide zoned heating to the web as it travels through the nip. For example, the rolls may be configured to have both heated and unheated regions so that as the web travels through the nip it is either heated on its upper and bottom surface by the heated regions of the rolls or is subjected to little or no heating by the unheated regions of the rolls. Alternatively, the rolls may be uniformly heated but comprise raised elements, that when opposed created a heated nip that selectively activates the web. The distance of web activated, as well as the necessary residence time for heat activation to occur, may be controlled by varying the design and rotational speed of the rollers 66.

In certain preferred embodiments upon activation the web of shell material 30 is allowed to retract at ambient temperatures as it passes into and out of the heat activation unit. This retraction can occur after the web travels from a first vacuum drum in the heating section to any subsequent drum and advantageously to a subsequent vacuum drum in the quenching section. After this additional retraction has occurred the web may be cooled on the quench vacuum roll(s) to preserve this retracted state as the web is processed further. Additionally, the material can be collected and rolled up on a take-up roller at a temperature at or below the quench roll temperature and above ambient temperature. During heat activation, generally the web of shell material 30 can be retracted from about 15 to about 55%. Preferably the web of shell material 30 can be retracted from about 25 to about 45%. Most preferably the web of shell material 30 can be retracted about 35%. Retraction can occur between one or more of the rollers 66.

After heat activation, components such as an ATL 32 or an absorbent component 40 are attached to the inelastic regions 60 of the web. The components may be attached using any method known in the art, for example, pressure bonding, adhesive bonding, thermal bonding and ultrasonic welding. Once the components are attached to form a composite web, individual body adhering absorbent articles 20 are die cut from the composite web 53. As a result of this configuration the components are laminated to nonactivated, non-stretchable portions of the web so that when the individual body adhering absorbent articles 20 are die cut from the composite web 53 there will be little or no residual stretch in the shells laminated regions which will reduce or eliminate curl in the individual body adhering absorbent article 20.

In an alternative embodiment, individual body adhering absorbent articles 20 may be manufactured as described above, however, the components such as an ATL 32 or an absorbent component 40 are attached to a web 30 having heat activatable elastic zones prior to activation. The components may be attached using any method known in the art, for example, adhesive bonding, pressure bonding, thermal bonding and ultrasonic welding. Once the components are attached to form a composite web, regions between the components are heat activated. After activation, individual body adhering absorbent articles 20 are die cut from the composite web 53. As a result of this configuration the components are laminated to nonactivated, non-stretchable portions of the web so that when the individual body adhering absorbent articles are die cut from the composite web there will be little or no residual stretch in the shells laminated regions which will reduce or eliminate curl in the individual body adhering absorbent article.

Figure 12:
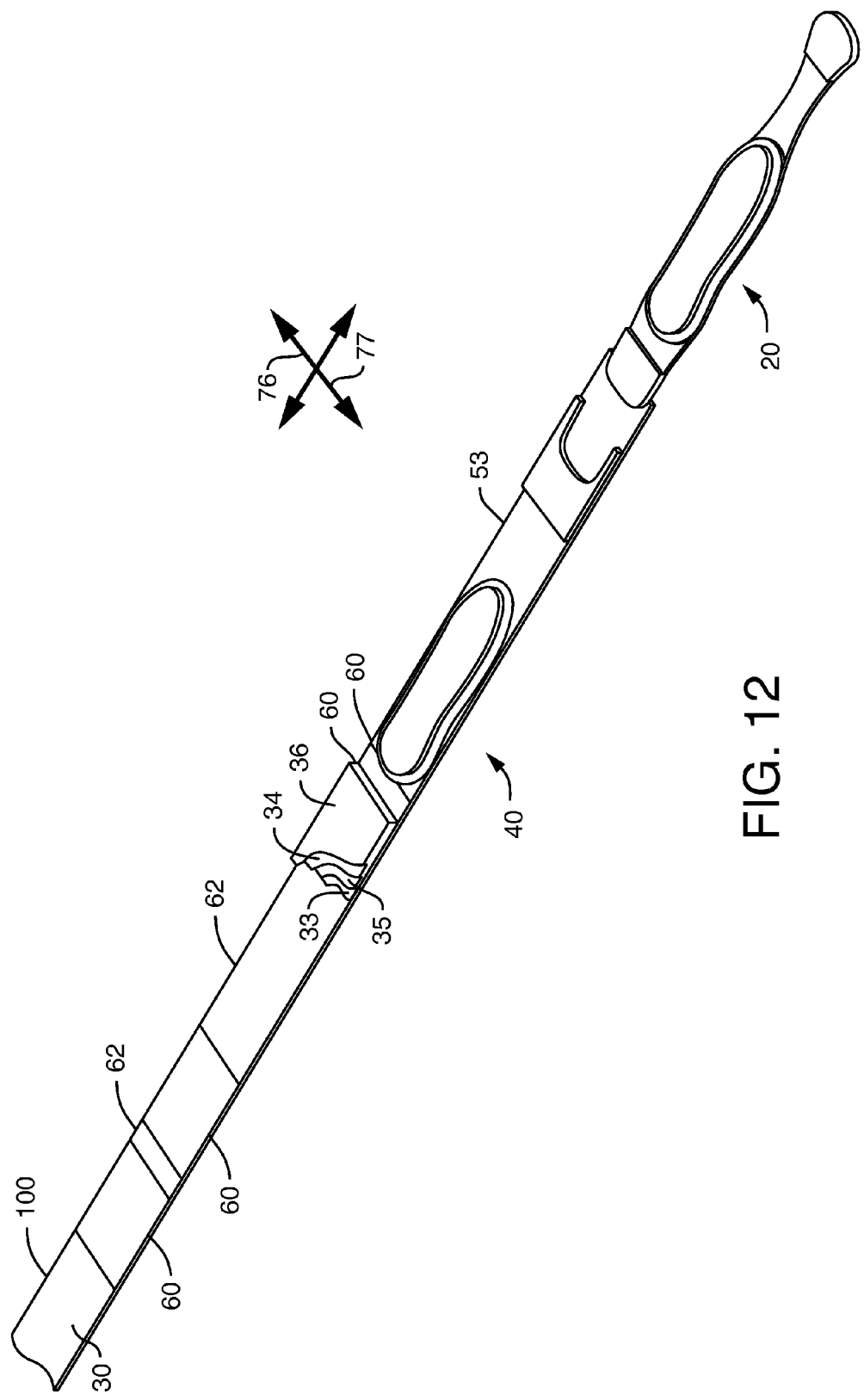
FIG. 12 shows a machine direction method of manufacturing a body adhering absorbent article according to still another embodiment of the present disclosure.

In yet another embodiment illustrated in FIG. 12 a body adhering absorbent article 20 may be manufactured using a multi-segmented film web 100 having alternating elastic and inelastic regions. Exemplary multi-segmented film webs include webs prepared as described in U.S. application Ser. No. 12/649427, filed Dec. 30, 2009, the contents of which are incorporated herein in a manner consistent with the present disclosure. For example, a multi-segmented film web may be provided having segments that stretch of from about 0 to about 25% in the machine direction and other segments that stretch from about 50 to about 100% in the machine direction. Preferably the multi-segmented film is laminated to one or more additional films and/or fabrics. For example, the apertured multi-segmented film described herein is bonded to a nonwoven web, which may be either a single layer nonwoven web or a multilayer nonwoven laminate that includes at least one layer of a nonwoven web or multiple nonwoven layers such as, for example, a three layered laminate comprising spunbond/meltblown/spunbond. The particular composition of any additional layers attached to the multi-segmented film may be selected to achieve desired attributes such as, for example, aesthetics, strength, and durability. The multi-segmented film and other fabric(s) can be laminated together to form a particular embodiment of shell material 30 by means known to those skilled in the art such as, for example, by pressure bonding, thermal bonding, ultrasonic bonding, adhesive bonding and the like.

Where one or more of the segments within the multi-segmented film comprises an elastic segment, any additional layers laminated thereto desirably comprise an extensible material or fabric. In this regard, the additional layer or layers can comprise, as examples, extensible nonwoven materials (e.g., creped nonwovens or nonwovens comprising highly crimped fibers), meshed fabrics, loosely woven fabrics, elastic composite materials and/or other like materials. Desirably the fabric comprises one or more layers of thermoplastic fibers which are elastic, inherently extensible or which have been treated so as to become extensible and/or elastic and which also have a cloth-like hand and drape. The composition of the thermoplastic polymer may be selected as desired to achieve a material having the desired physical attributes such as, for example, elasticity, hand, tensile strength, cost and so forth. Further, the outer nonwoven layer may be treated such as, for example, by embossing, hydroentangling, mechanically softening, printing, anti-static treatment or treated in some other manner in order to achieve desired aesthetics and/or functional characteristics.

Components such as an ATL 32 or an absorbent article 40 are attached to the inelastic regions 60 of the shell web 30. The components may be attached using any method known in the art, for example, pressure bonding, adhesive bonding, thermal bonding and ultrasonic welding. Once the components are attached to form a composite web, individual body adhering absorbent articles are die cut from the composite web 53. As a result of this configuration the components are laminated to nonactivated, non-stretchable portions of the web so that when the individual body adhering absorbent articles are die cut from the composite web there will be little or no residual stretch in the shells laminated regions which will reduce or eliminate curl in the individual body adhering absorbent article.

Figure 13:
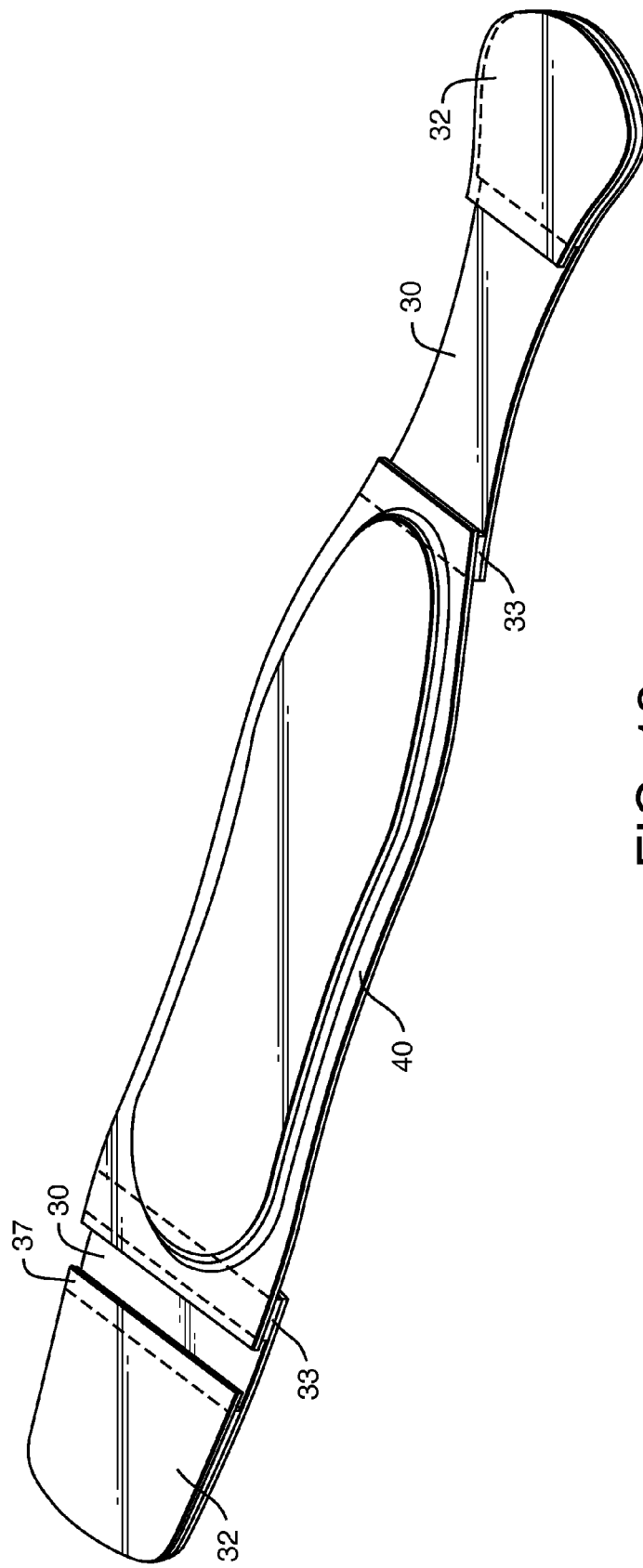
FIG. 13 shows a multi-segmented body adhesive absorbent article according to yet another embodiment of the present disclosure, the present disclosure provides methods of manufacturing a machine direction oriented multi-segmented body adhesive absorbent article.

In still another embodiment a body adhering absorbent article having a segmented shell may be manufactured to reduce curl. As illustrated in FIG. 13, a body adhering absorbent article may be manufactured by joining multiple segments with each segment having a component such as an ATL 32 or absorbent 40 attached thereto. The segments may be either elastic or inelastic depending on the components to be attached and the desired functionality and performance. For example, in one embodiment absorbent components 40 are attached to an inelastic material, for example a web of shell material that stretches less than about 25% in the longitudinal direction, for example from about 5 to about 10% in the longitudinal direction. Other segments 30 are stretchable in the longitudinal direction, preferably being stretchable from about 50 to about 100% in the longitudinal direction. Preferably each segment has little or no stretch in the lateral direction. The segments are preferably arranged such that the distal ends of the absorbent article comprise segments having from about 50 to about 100% stretch in the longitudinal direction, while the interior portion of the web comprises one or more segments having from about 0 to about 25% stretch in the longitudinal direction.

Preferably the shell materials are laminates comprising two or more films and/or fabrics. For example, the shell materials comprising the multi-segmented article may be bonded to a nonwoven web, which may be either a single layer nonwoven web or a multilayer nonwoven laminate that include at least one layer of a nonwoven web or multiple nonwoven layers such as, for example, a three layered laminate comprising spunbond/meltblown/spunbond. The particular composition of any additional layers attached to the multi-segmented film may be selected to achieve desired attributes such as, for example, aesthetics, strength, and durability. The multi-segmented film and other fabric(s) can be laminated together by means known to those skilled in the art such as, for example, by pressure bonding, thermal bonding, ultrasonic bonding, adhesive bonding and the like.

Where one or more of the segments within the multi-segmented article comprises an elastic segment, any additional layers laminated to the shell material desirably comprise an extensible material or fabric. In this regard, the additional layer or layers can comprise, as examples, extensible nonwoven materials (e.g., creped nonwovens or nonwovens comprising highly crimped fibers), necked nonwovens, meshed fabrics, loosely woven fabrics, elastic composite materials and/or other like materials. Desirably the fabric comprises one or more layers of thermoplastic fibers which are elastic, inherently extensible or which have been treated so as to become extensible and/or elastic and which also have a cloth-like hand and drape. The composition of the thermoplastic polymer may be selected as desired to achieve a material having the desired physical attributes such as, for example, elasticity, hand, tensile strength, cost and so forth.

Further, the outer nonwoven layer may be treated such as, for example, by embossing, hydroentangling, neck stretching, mechanically softening, printing, anti-static treatment or treated in some other manner in order to achieve desired aesthetics and/or functional characteristics.

Preferably components such as an absorbent structure 40 are attached to the inelastic segments, which are preferably in-turn attached to elastic segments having components such as an ATL 32. The various segments may be attached to one another using any method known in the art, for example, adhesive bonding, thermal bonding and ultrasonic welding. Once attached, the segments form a body adhering absorbent article. As a result of this configuration the components may be laminated to non-stretchable segments such that the resulting body adhering absorbent article has little or no residual stretch in the shells laminated regions which will reduce or eliminate curl in the individual body adhering absorbent article.

Accordingly, the multi-segmented body adhesive absorbent article illustrated in FIG. 13 may be manufactured such that the absorbent articles are oriented in the machine direction by forming two composite webs, each web having components oriented in the longitudinal direction attached thereto and then attaching the two composite webs together to form a third composite web, from which the absorbent article may be cut. For example, the first step may be supplying a web of elastic shell material attaching at least one component to the web of nonelastic shell material, such that the component is oriented in the longitudinal direction and forms a first composite web material. Then supplying a web of nonelastic shell material, attaching at least one component to the web of elastic shell material such that the component is oriented in the longitudinal direction and forms a second composite web material. The first composite web material may then be attached to the second composite web material to form a third composite material, which may be cut to form an absorbent article having a predetermined size and shape. The various components may be selected from, for example, an absorbent article, adhesive transfer layer, a barrier layer, a body adhering adhesive, an absorbent and containment flaps. The segments may be attached to one another using methods known in the art, for example, laminating, adhesive attachment, thermal bonding, pressure bonding or ultrasonic bonding. In certain preferred embodiments, such as that illustrated in FIG. 13, the multi-segmented body adhesive absorbent article may comprise three segments. In such instances the segments bearing the adhesive transfer layers 32 have an elastic shell material, while the segments bearing the absorbent 40 have nonelastic shell material. Other arrangements of segments and elastic and nonelastic shell materials, however, are contemplated and may be preferable depending on the desired composition and characteristics of the body adhering absorbent article.

Figure 15:
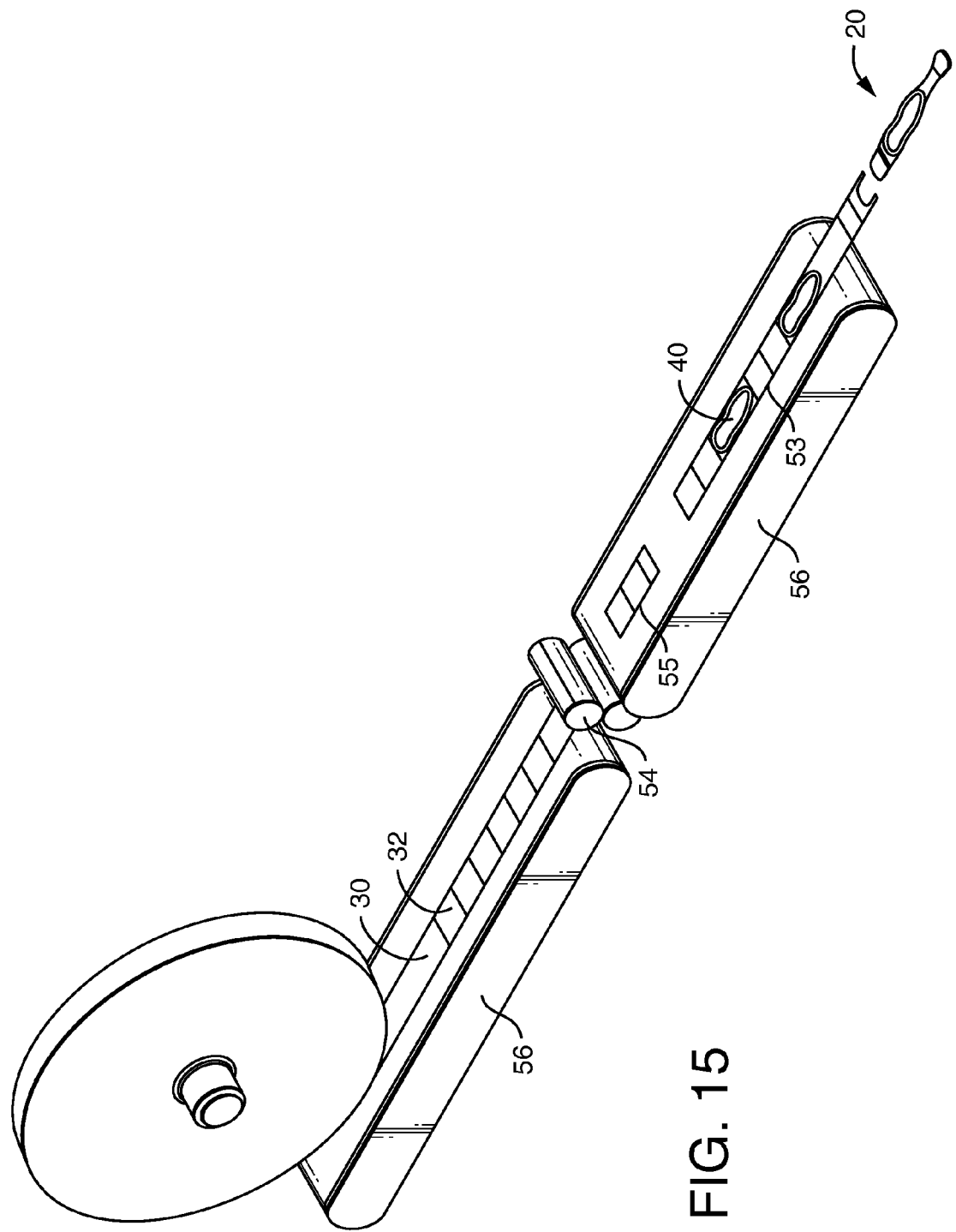
FIG. 15 shows still another embodiment for manufacturing a machine direction oriented body adhesive absorbent article and more particularly a machine direction oriented multi-segmented body adhesive absorbent article.

A particularly preferred method of manufacturing a machine direction oriented body adhesive absorbent article is illustrated in FIG. 15. Now with reference to FIG. 15, a web of shell material 30 is unwound onto a vacuum conveyor. Preferably the web shell is unwound onto the vacuum conveyor and maintained under little or no tension. Segments of ATL 32 are cut, rotated 90° and attached to the web of shell material 30. ATL 32 segments may be attached by methods known in the art, such as those disclosed herein. The attachment of the ATL 32 to the shell material 30 forms a first composite web, which is then cut into discrete panels 55 by a cutting apparatus 54. An absorbent component 40 is then attached to the discrete panel 55, preferably near the longitudinal ends of the panel 55, forming a second composite web 53. In certain embodiments the absorbent component 40 may be first attached to a web shell material to form an absorbent component-shell composite material from which individual absorbent components may be cut prior to attachment to the discrete panels. Once the absorbent component 40 is attached to the discrete panel 55 to form a second composite web 53, the second composite web 53 is cut to form a body adhering absorbent article 20.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

We claim:

1. A method of manufacturing a body adhering absorbent article oriented in the machine direction comprising:
   a. supplying an elastic web of shell material having a longitudinal and transverse direction;
   b. stretching the web of shell material in the longitudinal direction;
   c. deadening at least one region of the stretched web of shell material in the longitudinal direction to form a longitudinal deadened zone;
   d. attaching at least one component to at least a portion of the longitudinal deadened zone to form a composite web material; and
   e. cutting the composite web material to form an absorbent article having a predetermined size and shape.

2. The method of claim 1 wherein the components are selected from the group consisting of an adhesive transfer layer, an absorbent article, a banter layer, a body adhering adhesive, an absorbent and containment flaps.

3. The method of claim wherein the step of attaching comprises laminating, adhesive attachment, thermal bonding, pressure bonding or ultrasonic bonding.

4. The method of claim 1 wherein the step of deadening comprises bonding the stretched shell material in the transverse and/or longitudinal directions.

5. The method of claim 4 wherein bonding takes place by ultrasonic bonding, adhesive bonding, pressure bonding or thermal bonding.

6. A method of manufacturing body adhering absorbent article comprising:
   a. supplying a web of shell material
   b. attaching an adhesive transfer layer to the web of shell material to form a first composite web;
   c. cutting the first composite web to form discrete panels;
   d, attaching an absorbent component to the discrete panels to form a second composite web; and
   e. cutting the second composite we material to form an absorbent article having a predetermined size and shape.

7. The method of claim 6 wherein the web of shell material is unwound onto a vacuum conveyor, maintaining the web of shell material substantially without tension.

8. The method of claim 6 further comprising the step of rotating the adhesive transfer layer about 90° before attaching the adhesive transfer layer to the web of shell material.

* * * * *